(12) United States Patent
Wilcox et al.

(10) Patent No.: US 7,790,037 B2
(45) Date of Patent: Sep. 7, 2010

(54) SEPARATION OF COMPOUNDS USING TAGGING MOIETIES INCLUDING VARYING NUMBERS OF REPEAT UNITS

(75) Inventors: Craig S. Wilcox, Pittsburgh, PA (US); Dennis P. Curran, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 832 days.

(21) Appl. No.: 10/877,380

(22) Filed: Jun. 25, 2004

(65) Prior Publication Data

US 2005/0048541 A1 Mar. 3, 2005

Related U.S. Application Data

(60) Provisional application No. 60/482,430, filed on Jun. 25, 2003.

(51) Int. Cl.
*B01D 15/24* (2006.01)
*B01D 15/26* (2006.01)

(52) U.S. Cl. .................. 210/635; 210/668; 210/656; 210/198.2; 506/41

(58) Field of Classification Search .................. None
See application file for complete search history.

(56) References Cited

U.S. PATENT DOCUMENTS

| 5,777,121 | A | | 7/1998 | Curran et al. | |
|---|---|---|---|---|---|
| 5,859,247 | A | | 1/1999 | Curran et al. | |
| 6,040,297 | A | * | 3/2000 | De Flora et al. | 514/47 |
| 6,156,896 | A | | 12/2000 | Curran et al. | |
| 6,727,390 | B2 | | 4/2004 | Curran et al. | |
| 6,734,318 | B2 | | 5/2004 | Curran et al. | |
| 6,749,756 | B1 | * | 6/2004 | Curran et al. | 506/41 |

FOREIGN PATENT DOCUMENTS

WO   WO 01/61332   *   8/2001

OTHER PUBLICATIONS

Dumont et al (1995 J. Chromatography A 706:109-114).*
Kraus et al (1983 J. Chromatography 257:237-245).*
Thermo Hypersil-Keystone Fluorofix® Column Technical Guide (Downloaded Dec. 5, 2007).*
Cserhati et al (1997 J. Planar Chromatography 11:64-69).*
Jandera et al (1996 Chromatographia 42:539-546).*
Honigfort, M.E. et al., Use of Precipitons for Copper Removal in Atom Transfer Radical Polymerization; Macromolecules, 2002, vol. 35, No. 13, pp. 4849-4851.
Yan, B., Monitoring the Progress and the Yield of Solid-Phase Organic Reactions Directly on resin Supports; Acc. Chem. Res., 1998, 31, pp. 621-630.
Han, H.; Wolfe, M.M.; et al; Liquid-Phase Combinatorial Synthesis; Proc. Natl. Acad. Sci. USA, 1995, vol. 92, pp. 6419-6423.

Gravert, D.J. and Janda, K.D., "Organic Synthesis on Soluble Polymer Supports: Liquid-phase Methodologies," Chem. Rev., 1997, 97, pp. 489-509.
Pirrung, M.C.; Chen, J., Preparation and Screening against Acetylcholinesterase of a Non-Peptide "Indexed" Combinatorial Library; J. Am. Chem. Soc., 1995, 117, pp. 1240-1245.
Pirrung, M.C.; et al Discovey of a Novel Tetrahydroacridine Acetylcholinesterase Inhibitor Through an Indexed Combinatorial Library, Chem. Biol., 1995, vol. 2, No. 9, pp. 621-626.
Cheng, S.; Tarby, C.M.; et al. A Solution-Phase Strategy for the Synthesis of Chemical Libraries Containing Small Organic Molecules: A Universal and Dipeptide Mimetic Template; Bio. Med. Chem., 1996, vol. 4, No. 5; pp. 727-737.
Cheng, S.; Comer, D.D.; Williams, J.P.; et al.; Novel Solution Phase Strategy for the Synthesis of Chemical Libraries Containing Small Organic Molecules, J. Am. Chem. Soc., 1996, pp. 2567-2573.
Boger, D.L.; Tarby, C.M.; et.al; Generalized Dipeptidomimetic Template:Solution Phase Parallel Synthesis of Combinatorial Libraries; J. Am. Chem. Soc., 1996, 118, 2109-2110.
Bosanac, T.; Yang, et al.; Precipitons—Funtional Protecting Groups to Facilitate Product Separation: Applications in Isoxazoline Synthesis; Angew. Chem. Int. Ed., 2001, 40, No. 10; pp. 1875-1879.
Bosanac, T.; Wilcox, C.S.; A Photoactivated Precipiton for Reagent Sequestration in Solution-Phase Synthesis; J. Am. Chem. Soc., 2002, 124, pp. 4194-4195.
Luo, Z; Zhang, Q.; Oderaotoshi, Y.; Curran, D.P., Fluorous Mixture Synthesis: A Fluorous-Tagging Strategy for the Synthesis and Separation of Mixtures of Organic Compounds; Science, 2001, vol. 291, pp. 1766-1769.
Curran, D.P.; Oderaotoshi, Y., Thiol Additions to Acrylates by Fluorous Mixture Synthesis: relative Control of Elution Order in Demixing by the Fluorous Tag and the Thiol Sybstituent; Tetrahedron, 2001, 57, pp. 5243-5253.
Curran, D.P.; Furukawa, T., Simultaneous Preparation of Four Truncated Analogues of Discodermolide by Fluorous Mixture Synthesis; Org. Lett., 2002, vol. 4, No. 13, pp. 2233-2235.
Zhang, Q.; Rivkin, A.; Curran, D.P.; Quasiracemic Synthesis: Concepts and Implementation with a Fluorous Tagging Strategy to make Both Enantiomers of Pyridovericin and Mappicine; J. Am. Chem. Soc., 2002, 124, pp. 5774-5781.
Danielson, N.D. et al., "Fluoropolymers and Fluorocarbon Bonded Phases as Column Packings for Liquid Chromatography," J. Chromat., 1991, 544, pp. 187-199.

(Continued)

*Primary Examiner*—Christopher Low
*Assistant Examiner*—Christopher M Gross
(74) *Attorney, Agent, or Firm*—Bartony & Associates LLC

(57) ABSTRACT

A method of separating compounds, includes: a. tagging at least a first organic compound with a first tagging moiety to result in a first tagged compound; b. tagging at least a second organic compound with a second tagging moiety different from the first tagging moiety to result in a second tagged compound, the first tagging moiety and the second tagging moiety including at least one of a common repeat unit, but having a different number of the repeat units therein, the greater the number of repeat units, the greater the polarity of the tagging moiety; and c. separating the first tagged compound from a mixture including at least the second tagged compound using a chromatographic separation technique based upon differences in the number of repeat units between the first tagging moiety and the second tagging moiety.

19 Claims, 10 Drawing Sheets

OTHER PUBLICATIONS

Zhang, W.; Fluorous Synthesis of Heterocyclic Systems; Chem. Rev. 2004, 104, pp. 2531-2556.

Curran, D. P.; Fluorous Reverse Phase Silica Gel. A New Tool for Preparative Separations in Synthetic Organic and Organofluorine Chemistry; Synlett 2001, No. 9; pp. 1488-1496.

Gokel, G. W.; Dishong, D. M.; Diamond, C., J.; Lariat Ethers. Synthesis and Cation Binding of Macrocyclic Polyethers Possessing Axially Disposed Secondary Donor Groups; J.C.S.Chem. Comm., 1980, 22, pp. 1053-1054.

Chan, L.L.; Wong, K.H.; Smid, J., Complexation of Lithium, Sodium, and Potassium Carbanion Pairs with Polyglycol Dimethyl Ethers (Glymes). Effect of Chain Length and Temperature; J. Am. Chem. Soc., 1970, 92, pp. 1955-1963.

Schaus, S. E.; Brandes, B. D.; et al; Highly Selective Hydrolytic Kinetic Resolution of Terminal Epoxides Catalyzed by Chiral (salen)Co Complexes. Practical Synthesis of Enantioenriched Terminal Epoxides and 1,2-Diols; J. Am. Chem. Soc. 2002, vol. 124, No. 7, pp. 1307-1315.

Martinelli, M. J.; et al; Dibutyltin Oxide Catalyzed Selective Sulfonylation of alpha-Chelatable Primary Alcohols; Org. Lett, 1999, vol. 1, No. 3, pp. 447-450.

White, J. D.; et al., Degradation and Absolute Configurational Assignment to C34-Botryococcene; J. Org. Chem. 1992, 57, pp. 4991-4998.

Schaus, S.E.; et al., Total Synthesis of Muconin by Efficient Assembly of Chiral Builinding Blocks; J. Org. Chem. 1998, 63, pp. 4876-4877.

Zhang, W.; Fluorous Technologies for Solution-Phase High-Throughput Organic Synthesis; Tetrahedron, 2003, 59, pp. 4475-4489.

Zhang, W.; Luo, Z. et.al.; Solution-Phase Preparation of a 560-Compound Library of Individual Pure Mappicine Analogues by Fluorous Mixture Synthesis; J. Am. Chem. Soc. 2002, 124, pp. 10443-10450.

Zhang, Q.; Lu, H. et.al.; Fluorous Mixture of Stereoisomer Libraries: Total Synthesis of (+)-Murisolin and Fifteen Diastereoisomers; J. Am. Chem. Soc. 2004,126, pp. 36-37.

Curran, D. P.; Amatore, M. et.al.; Synthesis and Reactions of Fluorous Carbobenzyloxy (FCbz) Derivatives of alpha-Amino Acids; J.Org. Chem. 2003, 68, pp. 4643-4647.

Zhang, W.; Fluorous Mixture Synthesis (FMS) of Enantiomers, Diastereomers, and Compounds Libraries; Arkivoc; 2004; pp. 101-109.

Curran, D. P.; Luo, Z.; Fluorous Synthesis with Fewer Fluorines (Light Fluorous Synthesis): Separation of Tagged from Untagged Products by Solid-Phase Extraction with Fluorous Reverse-Phase Silica Gel; J. Am. Chem. Soc., 1999, 121, pp. 9069-9072.

Curran, D. P.; Strategy-Level Separations in Organic Synthesis: From Planning to Practice; Angew. Chem., Int. Ed.; 1998, 37, pp. 1174-1196.

Curran, D. P. Fluorous Techniques for the Synthesis of Organic Molecules: A Unified Strategy for Reaction and Separation; Stimulating Concepts in Chemistry, Wiley-VCH: New York, 2000, 25-37.

Yoshida, J; Itami, K.; Tag Strategy for Separation and Recovery; Chem. Rev. 2002, 102, pp. 3693-3716.

Tzschucke, C.C.; Markert, C. et.al.; Modern Separation Techniques for the Efficient Workup in Organic Synthesis; Angew. Chem. Int. Ed. 2002, 41, pp. 3964-4000.

* cited by examiner

Fig. 7

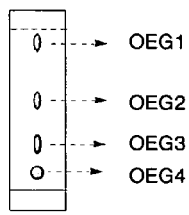

a) silica gel TLC analysis of the sixteen compound mixture bearing four OEG tags and four fluorous tags; pentane/ethyl acetate 1:1 (v/v) as eluant, UV visualization. Rf = 0.87 (OEG1, all four fluorous tags), 0.55 (OEG2, all four fluorous tags), 0.27 (OEG3, all four fluorous tags), 0.09 (OEG4, all four fluorous tags)

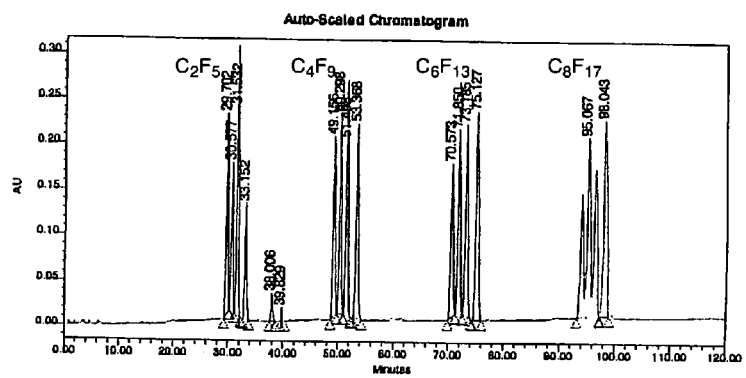

b) fluorous HPLC analysis of the sixteen compound mixture: A Waters Delta 600 pump, a Waters 600 controller and a Waters 2487 DAD were employed. A PF-C8 5-micron 150 x 4.6 mm S/N 2207014 PF-C8 Fluorous HPLC column (FTI) was used. Separations were conducted at room temperature, and solvents were purged with helium for 30 minutes before the first elution. The column was eluted under two linear gradients for 120 min. The first gradient started with 40% $CH_3CN$/60% $H_2O$ and ended with 80% $CH_3CN$/20% $H_2O$ in 90 min and then up to 90% $CH_3CN$/10% $H_2O$ in another 30 min in the second gradient. The flow rates in both gradients are 1mL/min. The compounds elute primarily by order of fluorous tag with a secondary separation by OEG tag (OEG4 before OEG3 before OEG2 before OEG1). The small peaks at 38 and 39 min are minor impurities derived from one of the starting compounds.

— 1 —

SEPARATION OF COMPOUNDS USING TAGGING MOIETIES INCLUDING VARYING NUMBERS OF REPEAT UNITS

CROSS-REFERENCE TO RELATED APPLICATION

The present application claims benefit of U.S. Provisional Patent Application Ser. No. 60/482,430, filed Jun. 25, 2003, the disclosure of which is incorporated herein by reference.

BACKGROUND OF THE INVENTION

The present invention relates to the separation of compounds using tagging moieties including varying numbers of repeat units, and particularly, to the use of tagging moieties including repeat units that increase affinity of the tag for a stationary support (by, for example, changing the polarity, the hydrophilicity, the lipophilicity, or the charge of the tag) in a stepwise manner as the number of repeat units increases.

References set forth herein may facilitate understanding of the present invention or the background of the present invention. Inclusion of a reference herein, however, is not intended to and does not constitute an admission that the reference is available as prior art with respect to the present invention.

Solid phase chemical synthesis methods revolutionized protein and polynucleotide synthesis and are now an important method for small molecule chemical discovery. The benefits of employing solid support methods include the ease of first-pass purification of the tethered products and the possibility of generating very large libraries through systematic diversification strategies. These benefits come with a cost, however. For example, reaction conditions that have been developed for homogeneous ("solution phase") reactions can require substantial re-optimization for use on solid supports. Also, some solution phase reactions are not transferable to solid phase because required temperatures and/or pressures, or the need to have rapidly diffusing reactive intermediates, may be incompatible with high molecular weight supports. See, for example, Honigfort, M. E.; Brittain, W. J.; Bosanac, T.; Wilcox, C. S. *Macromolecules*, 2002, 35, 4849-4851. Moreover, monitoring reaction progress and characterizing products still bound to the support is challenging. See, for example, Yan, B. *Acc. Chem. Res.*, 1998, 31, 621-630. Expensive, specialized equipment is often employed and scale-up of the optimized solid phase process may not be feasible.

To circumvent some of these difficulties with solid phase methods, researchers have pursued alternative solution phase methods such as liquid phase combinatorial synthesis, indexed combinatorial libraries, template-based libraries, precipitons, and fluorous mixture synthesis (FMS). See, for example, Han, H.; Wolfe, M. M.; Brenner, S.; Janda, K. D. *Proc. Natl. Acad. Sci. USA*, 1995, 92, 6419-6423. (b) Gravert, D. J.; Janda, K. D., *Chem. Rev.*, 1997, 97, 489-509; Pirrung, M. C.; Chen, J., *J. Am. Chem. Soc.*, 1995, 117, 1240-1245; Pirrung, M. C.; Chau, J. H-L.; Chen, J., *Chem. Biol.*, 1995, 2, 621-626; Cheng, S.; Tarby, C. M.; Comer, D. D.; Williams, J. P.; Caporale, L. H.; Myers, P. L.; Boger, D. L, *Bio. Med. Chem.*, 1996, 4, 727-737; Cheng, S.; Comer, D. D.; Williams, J. P.; Myers, P. L.; Boger, D. L., *J. Am. Chem. Soc.*, 1996, 118, 2567-2573; Boger, D. L.; Tarby, C. M.; Comer, D. D.; Myers, P. L.; Caporale, L. H., *J. Am. Chem. Soc.*, 1996, 118, 2109-2110; Bosanac, T.; Yang, J. M.; Wilcox C. S. *Angew. Chem. Int. Ed. Eng.*, 2001, 40, 1875-1879; Bosanac, T.; Wilcox, C. S. J. Am. Chem. Soc., 2002, 124, 4194-4195; Luo, Z; Zhang, Q.; Oderaotoshi, Y.; Curran, D. P., *Science*, 2001, 291, 1766-1769; Curran, D. P.; Oderaotoshi, Y., *Tetrahedron*, 2001, 57, 5243-5253; Curran, D. P.; Furukawa, T., *Org. Lett.*, 2002, 4, 2233-2235; Zhang, Q.; Rivkin, A.; Curran, D. P., *J. Am. Chem. Soc.*, 2002, 124, 5774-5781; and U.S. Pat. No. 6,749,756.

In several embodiments of fluorous mixture synthesis (as disclosed, for example, in U.S. Pat. No. 6,749,756), substrates attached to fluorous sorting tags of differing fluorous nature/fluorine content are mixed, taken through a certain number of reactions as a mixture, and demixed (that is, separated) using a fluorous separation technique. The fluorous mixture synthesis approach to accelerated chemical synthesis has significant promise. An enabling characteristic of fluorous tags used for chromatographic separations is the predictable incremental increase in retention time with increasing fluorocarbon chain length.

U.S. Pat. No. 6,749,756 also discloses a general tagging scheme wherein a mixture of tagged products is separated by a separation technique based upon or complementary to differences in the tagging moieties. In addition to tags which differ in fluorous nature, U.S. Pat. No. 6,749,756 further discloses separations using tags differing in total charge, tags differing in size (for example, oligomers, dendrimers and polymers of differing length), and tags differing in polarity (for example, linear hydrocarbons of differing lengths, which decrease in polarity with increasing length).

Given the benefit that tagging methodologies can bring to chemical synthesis and separation, it is desirable to develop additional and/or complementary tags and tagging methods.

SUMMARY OF THE INVENTION

In one aspect, the present invention provides a method of separating compounds, including the steps: a. tagging at least a first organic compound with a first tagging moiety to result in a first tagged compound; b. tagging at least a second organic compound with a second tagging moiety different from the first tagging moiety to result in a second tagged compound, the first tagging moiety and the second tagging moiety including at least one of a common repeat unit, but having a different number of the repeat units therein, the greater the number of repeat units, the greater the polarity of the tagging moiety; and c. separating the first tagged compound from a mixture including at least the second tagged compound using a chromatographic separation technique based upon differences in the number of repeat units between the first tagging moiety and the second tagging moiety.

The repeat unit can, for example, include at least one Lewis acid atom or group or at least one Lewis basic atom or group. The first tagging moiety and the second tagging moiety can be selected so that the order in which the first tagged compound and the second tagged compound separate is predetermined.

The first tagging moiety and the second tagging moiety can, for example, include between 1 and 100 repeat units, between 1 and 50 units, between 1 and 20 repeat units or between 1 and 5 repeat units. Tagging moieties used in the separations and reactions of the present invention can differ by only a single repeat unit or by multiple repeat units. The repeat units can, for example, form an amide linkage, an ether linkage, an amine linkage, a thioether linkage, a phosphine linkage, an ester linkage or a glycol linkage. In one embodiment, the repeat unit is an alkylene glycol repeat unit such as an ethylene glycol repeat unit. A third compound having no repeat units or even no tag can also be separated from the mixture using in the chromatographic separation technique.

An additive that interacts with the repeat units of the first tagging moiety and the second tagging moiety can be added to the stationary phase. In the case that the repeat unit is ethylene glycol, the additive can include a group IA cation. In one such embodiment, the additive includes a lithium cation.

At least one of the first tagged compound and the second tagged compound can also include a fluorous tagging moiety, and the method can further include a separation using a fluorous separation technique. The first tagged compound can also include a first fluorous tagging moiety and the second tagged compound can also include a second fluorous tagging moiety different from the first fluorous tagging moiety. The method further includes a separation using a fluorous separation technique.

At least one of the first tagged compound and the second tagged compound can also include an alternative or different type of tagging moiety adapted to be separated via a second type of separation technique other than a separation technique based upon differences in polarity. In this embodiment, the method further comprises a separation using the second type of separation technique. Likewise, the first tagged compound can include a first alternative tagging moiety adapted to be separated via a second type of separation technique other than a separation technique based upon differences in polarity. The second tagged compound can also include a second alternative tagging moiety (different from the first alternative tagging moiety). The second alternative tagging moiety is also adapted to be separated via the second type of separation technique. The method in this embodiment also includes a separation using the second type of separation technique.

The first tagging moiety and the first alternative tagging moiety can be attached to the first compound via a common group or atom. In one embodiment, the first tagging moiety and the first alternative tagging moiety are each attached to the common group which is attached to the first compound. In another embodiment, the first tagging moiety and the first alternative tagging moiety are attached to each other and one of the first tagging moiety and the first alternative tagging moiety is attached to the first compound via the common group or atom.

In another aspect, the present invention provides a method of separating compounds including the step of tagging a plurality of organic compounds with a plurality of tagging moieties to result in a plurality of tagged compounds. Each of the tagging moieties is different. Each of the tagging moieties includes at least one of a common repeat unit, but has a different number of the repeat units therein. The greater the number of repeat units, the greater the polarity of the tagging moiety. The method further includes separating at least one of the plurality of tagged compounds from other tagged compounds with a different tag via a separation technique based upon differences in the polarity of the tagging moieties of the tagged compounds.

In a further aspect, the present invention provides a method for carrying out a chemical reaction including the steps of tagging a plurality of compounds with different tagging moieties to create tagged compounds, and conducting at least one chemical reaction on the tagged compounds to produce a mixture of tagged products. Each the tagging moieties includes at least one of a common repeat unit, but has a different number of the repeat units therein. The greater the number of repeat units, the greater the polarity of the tagging moiety. The method further includes separating at least one of the plurality of tagged compounds from other tagged compounds with a different tagging moiety using a separation technique based upon differences in the polarity of the tagging moieties of the tagged compounds.

The method can further include the step of removing the tagging moieties from the tagged products. All of the tagged compounds can be reacted with a common reactant or reactants. Likewise, at least some of the tagged compounds can be reacted with different reactants.

A first plurality of compounds can be tagged with a first tagging moiety and mixed with other tagged compounds that are tagged with tagging moieties different from the first tagging moiety. The separation of the tagged products can provide mixtures of product compounds bearing the same initial tag. The tagged compounds can be selectively tagged with different tagging moieties such that the tagged products separate into fractions of known identity as determined by the tagging moieties.

At least one of the tagged products can also include a fluorous tagging moiety and the method can further include a separation using a fluorous separation technique. Likewise, a plurality of the tagged products can also include different fluorous tagging moieties and the method can further include a separation using a fluorous separation technique. In one embodiment, a plurality of the tagged compounds are reacted with a plurality of compounds comprising different fluorous tagging moieties and the method further comprises a separation using a fluorous separation technique.

At least one of the tagged products can also include an alternative tagging moiety adapted to be separated via a second type of separation technique other than a separation technique based upon differences in polarity. In this embodiment, the method further comprises a separation using the second type of separation technique. Likewise, a plurality of the tagged products can also include unique or different alternative tagging moiety adapted to be separated via a second type of separation technique other than a separation technique based upon differences in polarity. In one embodiment, a plurality of the tagged compounds are reacted with a plurality of compounds including different alternative tagging moieties adapted to be separated via a second type of separation technique other than a separation technique based upon differences in polarity.

In another aspect, the present invention provides a method of separating compounds including the steps of: a. tagging a first organic compound with a first tagging moiety to result in a first tagged compound; b. tagging at least a second organic compound with a second tagging moiety different from the first tagging moiety to result in a second tagged compound, the first tagging moiety and the second tagging moiety including at least one of a common repeat unit, but having a different number of the repeat units therein, the greater the number of repeat units, the greater the polarity of the tagging moiety; and c. separating the first tagged compound into a predetermined fraction from a mixture including at least the second tagged compound using a separation technique based upon differences in polarity between the first tagging moiety and the second tagging moiety, wherein the predetermined fraction and the identity of the first tagged compound in the predetermined fraction are determined by the first tagging moiety.

In a further aspect, the present invention provides a method of separating compounds including the step of tagging a plurality of organic compounds with a plurality of tagging moieties of a first type to result in a plurality of tagged compounds. Each of the tagging moieties of the first type is different. The method further includes tagging the plurality of the tagged compounds with a plurality of tagging moieties of at least a second type to result in a plurality multiply tagged compounds. Each of the tagging moieties of the second type is different. The method also includes performing a first separation based upon differences in the first type of tagging moieties and performing at least a second separation based upon differences in the second type of tagging moieties. The first separation and the second separation can be performed sequentially. The first separation and the second separation can also be performed generally simultaneously.

In another aspect, the present invention provides a method for carrying out a chemical reaction including the steps of: tagging a plurality of compounds with different tagging moieties of a first type and with different tagging moieties of at least a second type to create multiply tagged compounds. The method further includes conducting at least one chemical reaction on the multiply tagged compounds to produce a mixture of multiply tagged products, performing a first separation based upon differences in the first type of tagging moieties, and performing at least a second separation based upon differences in the second type of tagging moieties to separate the multiply tagged compounds.

In another aspect, the present invention provides a method for carrying out a chemical reaction including the steps of: tagging a plurality of compounds with different tagging moieties of a first type to result in a plurality of tagged compounds, reacting the plurality of tagged compounds with a plurality of compounds tagged with different tagging moieties of a second type to create multiply tagged compounds, performing a first separation based upon differences in the first type of tagging moieties, and performing at least a second separation based upon differences in the second type of tagging moieties to separate the multiply tagged compounds.

In a further aspect, the present invention provides a method of separating compounds including: a. tagging at least a first organic compound with a first nonfluorous tagging moiety to result in a first tagged compound; b. tagging at least a second organic compound with a second nonfluorous tagging moiety different from the first tagging moiety to result in a second tagged compound, the first nonfluorous tagging moiety and the second nonfluorous tagging moiety including at least one of a common repeat unit, but having a different number of the repeat units therein, the greater the number of repeat units, the greater the affinity of the nonfluorous tagging moiety for a stationary phase of a chromatographic separation technique; and c. separating the first tagged compound from a mixture including at least the second tagged compound using a chromatographic separation technique based upon differences in the number of repeat units between the first nonfluorous tagging moiety and the second nonfluorous tagging moiety.

In still a further aspect, the present invention provides a method for carrying out a chemical reaction including the steps of: tagging a plurality of compounds with different nonfluorous tagging moieties to create tagged compounds and conducting at least one chemical reaction on the tagged compounds to produce a mixture of tagged products. Each the tagging moieties includes at least one of a common repeat unit, but has a different number of the repeat units therein. The greater the number of repeat units, the greater the affinity of the tagging moiety for a stationary phase of a chromatographic separation technique. The method further includes separating at least one of the plurality of tagged compounds from other tagged compounds with a different tagging moiety via the chromatographic separation technique based upon differences in the affinity the tagging moieties of the tagged compounds.

As used herein, the term "tagging" refers generally to attaching a moiety or group (referred to as a "tagging moiety" or "tagging group") to a compound to create a "tagged compound". Preferably, the tagging moiety is attached via a covalent bond. However, other strong attachments such as ionic bonding or chelation can also be used. In the present invention, different tagging moieties are preferably used on different compounds to facilitate separation of such tagged compounds.

If compounds that are tagged are to undergo one or more reactions to produce tagged product compounds that are to be separated, the tagging moieties preferably do not substantially interfere with the reaction(s) and are not cleaved during the reaction(s). In that regard, the product compounds must be tagged to achieve separation based upon differences in the tagging moiety. In this embodiment, the tags can also function as protecting groups. As will be discussed further below, the manner/order of steps in which the tagged product compounds become tagged is does not affect the ultimate separation.

In the case that fluorous tagging moieties are used in conjunction with the polar or other tagging moieties of the present invention, the fluorous tagging moieties differ in fluorous nature (for example, fluorine content and/or structure) as described in U.S. Pat. No. 6,749,756. As used herein, the term "fluorous", when used in connection with an organic (carbon-containing) molecule, moiety or group, refers generally to an organic molecule, moiety or group having a domain or a portion thereof rich in carbon-fluorine bonds (for example, fluorocarbons, fluorohydrocarbons, fluorinated ethers and fluorinated amines). The term "fluorous substrate," thus refers generally to a substrate comprising a portion rich in carbon-fluorine bonds. As used herein, the term "perfluorocarbons" refers generally to organic compounds in which all hydrogen atoms bonded to carbon atoms have been replaced by fluorine atoms. The terms "fluorohydrocarbons" and "hydrofluorocarbons" include organic compounds in which at least one hydrogen atom bonded to a carbon atom has been replaced by a fluorine atom. Preferred fluorohydrocarbons and fluorohydrocarbon groups for use in the present invention have approximately two or more fluorines for every hydrogen. The attachment of fluorous moieties to organic compounds and the separation of compounds based upon differences in fluorous nature of such fluorous tagging moieties are discussed in U.S. Pat. Nos. 6,749,756, 6,734,318, 6,727,390. 6,156,896, 5,859,247, and 5,777,121, the disclosures of which are incorporated herein by reference.

As known in the art, compounds tagged with fluorous moieties can be separated using a fluorous separation technique (for example, fluorous chromatography). As used herein, the term "fluorous separation technique" refers generally to a method that is used to separate mixtures containing fluorous molecules or organic molecules bearing fluorous domains or tags from each other based predominantly on the fluorous nature of molecules (for example, size and/or structure of the fluorous molecule or domain). Fluorous separation techniques include but are not limited chromatography over solid fluorous phases such as fluorocarbon bonded phases or fluorinated polymers. See for example, Danielson, N. D. et al., "Fluoropolymers and Fluorocarbon Bonded Phases as Column Packings for Liquid Chromatography," *J. Chromat.*, 544, 187-199 (1991). Examples of suitable fluorocarbon bonded phases include commercial Fluofix® and Fluophase™ columns available from Keystone Scientific, Inc. (Bellefonte, Pa.), FluoroSep™-RP-Octyl from ES Industries (Berlin, N.J.) and FluoroFlash™ available from Fluorous Technologies, Inc. (Pittsburgh, Pa.). Other fluorous separation techniques include liquid-liquid based separation methods such as countercurrent distribution with a fluorous solvent and an organic solvent.

As used herein, the terms, "oligomers" and "polymers" refer generally to molecules that are made by linking together repeating units of one or more small molecules called monomers. Generally, oligomers include fewer monomer units than polymers, although the precise border between an oligomer and a polymer in not well defined. As used herein, the term "dendrimer" refers generally to branched or hyperbranched molecules that are synthesized in generations by attachments of successive sets of building blocks to a core (or the inverse). See, for example, *Dendrimers*, F. Vogtle, Ed., Springer-Verlag Berlin: Heidelberger Platz 3/W-1000 Berlin 33/Germany, 1-18 (1998). In the present invention, so-called "soluble" oligomers. polymers and dendrimers are preferred. Soluble polymers are discussed in, for example, Gravert, D. J. and Janda, K. D., "Organic Synthesis on Soluble Polymer Supports: Liquid-phase Methodologies," *Chem. Rev.*, 97, 489-509 (1997). Through use of soluble tags, substrates or products can be attached to tags having differing numbers of repeat units, and then the tagged substrates can be mixed to generate a true mixture which can, if desired, be reacted in standard solution phase organic reactions prior to separation.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 7 illustrates an analytical HPLC trace of the a mixture of the 16 compound of FIG. 6 on a FluoroFlash PF-C8 column.

DETAILED DESCRIPTION OF THE INVENTION

Figure 1A:
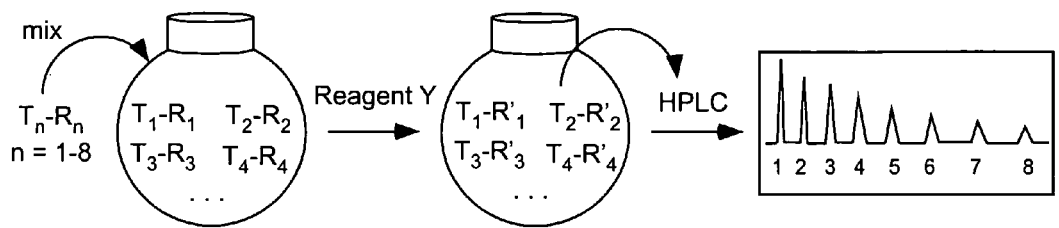
FIG. 1A illustrates one embodiment of a reaction and subsequent separation of compounds tagged with tagging moieties of the present invention.

In general, the present invention provides tags including differing numbers of a repeat unit which impart affinity for a stationary support (for example, by imparting polarity) to the tag. The greater the number of repeat units, the greater the affinity the tag exhibits for the stationary phase. In one embodiment of the present invention, a plurality of molecules, $R^N$, are labeled prior to or during chemical processing to afford tagged molecules having the formula $R^N$—Z—(—U—)$_N$—W, where N is an integer. N is preferably in the range of 1-100, more preferably in the range of 1-50, and most preferably in the range of 1-20. $R^N$ represents the general molecular entities to be separated. U represents a repeat unit that imparts affinity for a stationary support (for example, polarity) to the tag. U, can for example, have the general formula

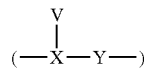

wherein Y represents a linking functional group or atom in the backbone of the tag, which may or may not be present. In one representative embodiment, Y can impart polarity to the repeat unit. Polar interactions include, for example, hydrogen bonding, Lewis acid-base interactions, metal-ligand interactions, ionic bonds, and covalent bonding. In other embodiments of the present invention, Y (and repeat unit U generally) can, for example, impart hydrophilicity, lipophilicity, or charge to the tag. In the case that U imparts polarity, Y can, for example, be O, B, N, S, or P. X can, for example, be a carbon-containing component (for example, an alkylene group —(CH$_2$)$_a$—, wherein a is an integer).

V represents a side chain or group that may or may not be present. V can, for example, improve the separation by, for example, imparting polarity (or other affinity) to the repeat unit and thus to the tag. In the case that, for example, U imparts polarity and Y is not present (for example, in the case that X represents a simple carbon chain as in polyethylenes, polypropylenes, or polystyrenes), V is preferably present and imparts polarity to repeat unit U. In the case that U imparts polarity, V can, for example, include an ether group, an amine group, an imine group, an ester group, a sulfide group, a sulfoxide group, a sulfone group, a heterocyclic group, a phosphine group or a group including one or more such groups.

Multiple side chain groups V can be present. In that regard, a plurality of short chains (for example, 1-5 backbone atoms in length) of a group with a particular type of affinity for a complementary stationary phase can be attached/repeated over the length oligomeric backbone. For example, hydrophobic side chains can be present on a hydrophilic oligomer to create tags suitable for use with reverse phase columns. Each hydrophobic side chain unit increases the net hydrophobicity or lipophilicity of the tag, resulting in a desirable stepwise increase in retention time during separation of tagged compound including tags having different numbers of hydrophobic side chains.

X and Y together can, for example, form a repeat unit of 1-10 or 1-5 atoms in length. X and/or Y can include one or more side chains or groups which may or may not affect the affinity of the repeat unit for a stationary phase. V can, for example, be 1-10 or 1-5 atoms in length. V can also include one or more side chains or groups which may or may not affect the affinity of the repeat unit for a stationary phase.

W represents a terminating group on the chain. W can be inert or can be chosen to improve the separation and/or the detection of the molecules during the separation. Z represents a connecting group or spacer, which can be present or absent. As clear to one skilled in the art, the tagging moieties of the present invention can be oligomers, polymers or dendrimers as defined above. As described further below, mixtures of tagged compounds of the present invention can be reliably and predictably separated to provide the N pure products. One of the separated products can also have no tag or a tag with no repeat units (N=0), thereby enabling separation of N+1 different products. A tag with no repeat units can be referred to as a "null tag."

In a representative embodiment of the present invention, tags including alkylene glycols repeat units were used to separate 18 different molecules in a single chromatographic step. In such molecules and related molecules, X is a carbon-based group such as an alkylene group $(CH_2)_a$ and Y is oxygen O. In several experiments, oligoethylene glycols that were end-capped and linked to target molecules by an ester linkage were used. The oligoethylene glycols had the general formula:

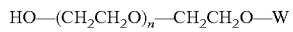

In such molecules, Z is O and U is $CH_2CH_2O$ (wherein, X is $(CH_2CH_2)$ and Y is O). V is absent in such molecules.

This new general category of molecular separating agents or tags are sometimes referred to herein as "oligomeric sorting tags", as the separating agents preferably had a core oligomer structure of 1-20 monomer units or repeat units. Indeed, separations were performed with separating tags having an oligomer structure of 1-5 repeat units. The oligomers can be made by standard methods of oligomer formation from suitably designed monomer units according to well known methods. The core structure may be prepared in a single oligomerization step or through stepwise construction. Examples of polar oligomeric sorting tags other than oligoalkylene glycols include oligoamides, oligoethers, oligoamines, oligothioethers, oligophosphines, or oligoesters. Likewise, polyalkylene glycols, polyamides, polyethers, polyamines, polythioethers, polyphosphines, or polyesters can also be used. As described above, polymers typically have more repeat units that oligomers, but the distinction is not well defined. The oligomers or polymers can be linear or branched. Dendrimers are thus also suitable for use in the present invention.

Figure 1B:
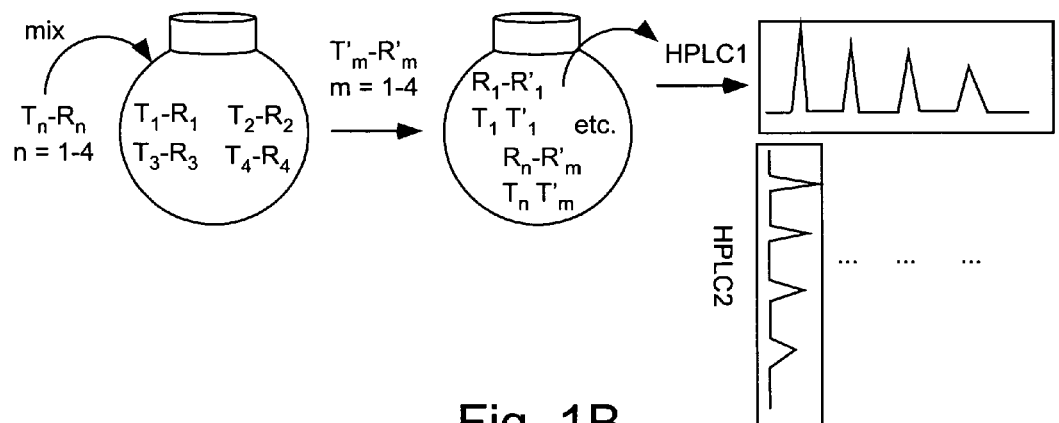
FIG. 1B illustrates one embodiment including reaction of a mixture of compounds tagged with a first type of tags with a mixture of compounds tagged with a second type of tags and subsequent separation of the resultant products which include tags of the first type and tags of the second type.
Figure 2:
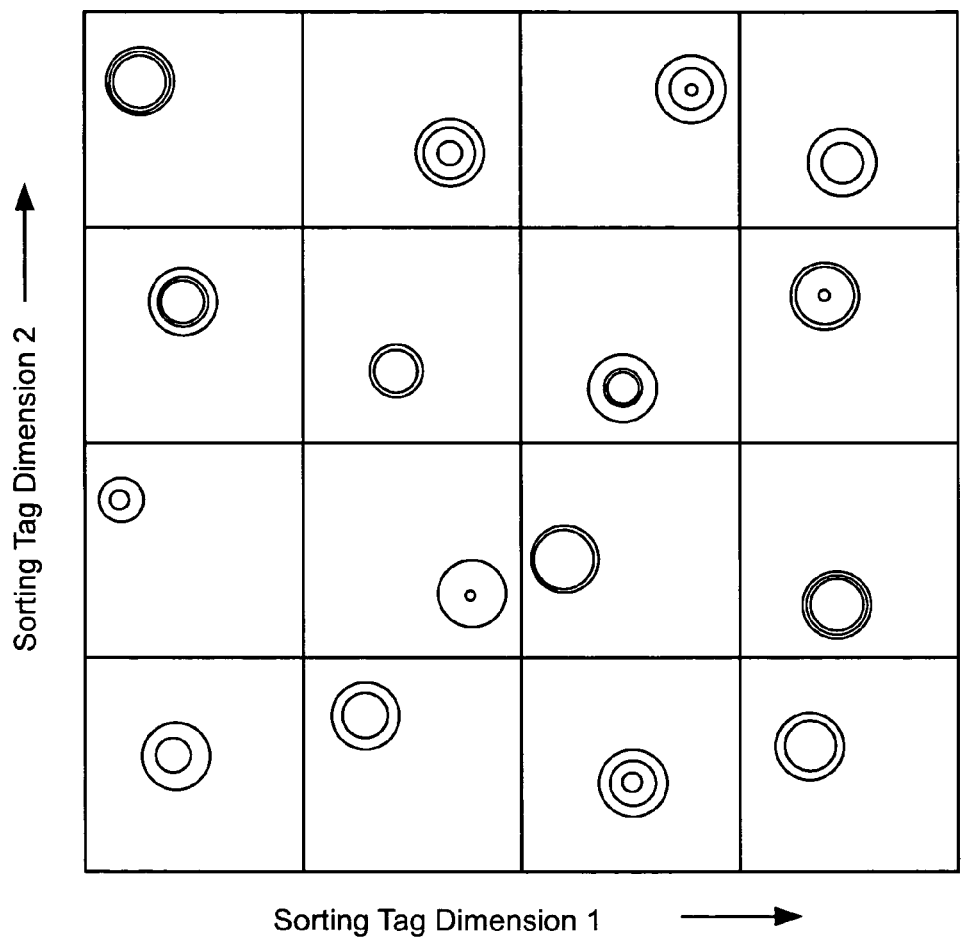
FIG. 2 illustrates a two-dimensional separation of the doubly tagged compounds of the reaction of FIG. 1B.
Figure 4:
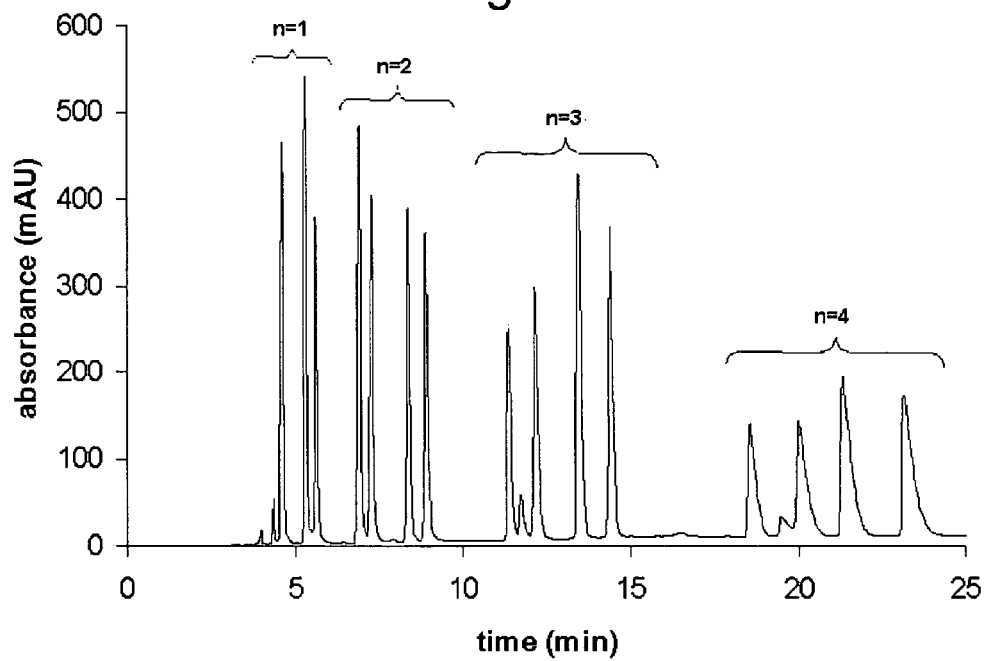
FIG. 4 illustrates separation of the esters of FIG. 3 on a 5μ Supelcosil column (Gradient: 3.7 EtOAc:Hex to 8.2 EtOAc: Hex in 20 minutes with a flowrate of 1 ml/min.).
Figure 8:
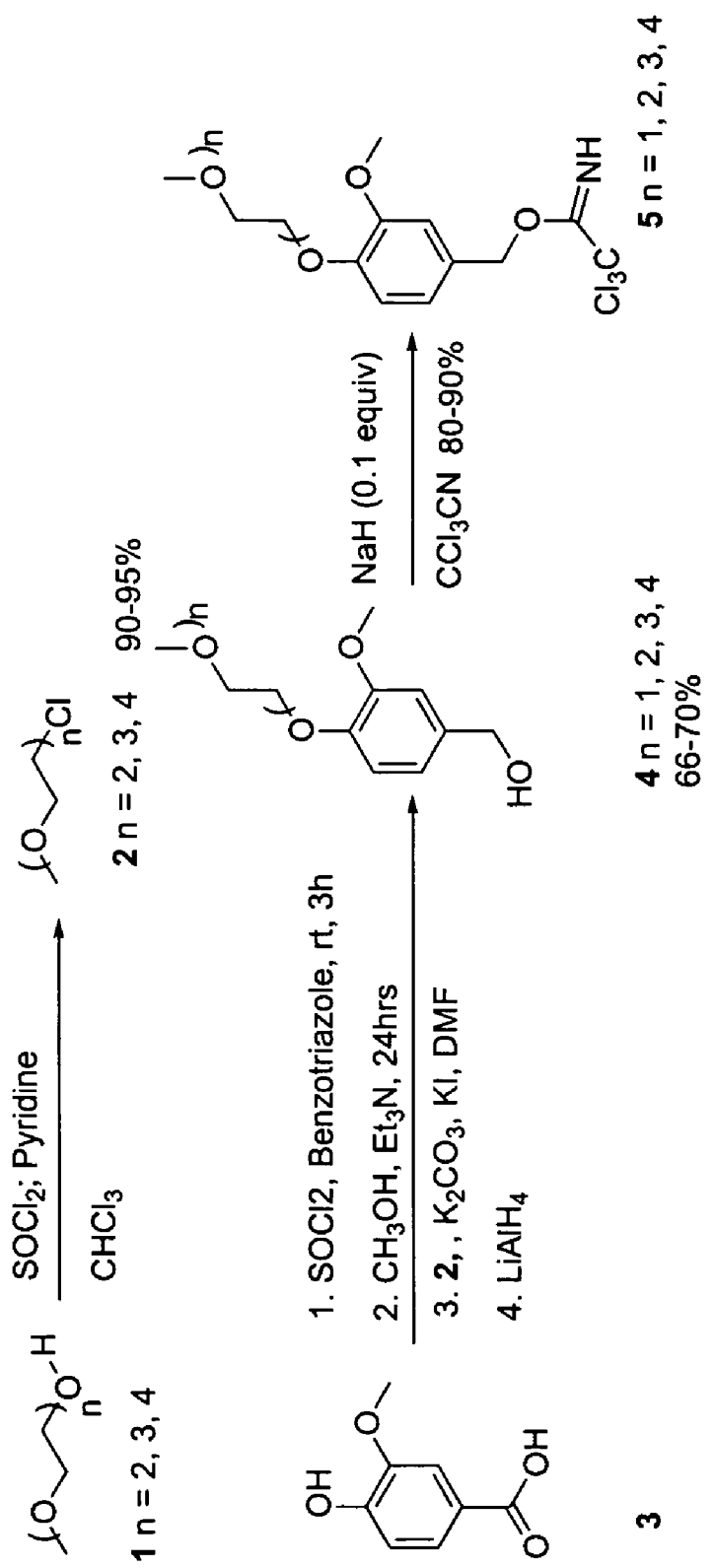
FIG. 8 illustrates the synthesis of several oligoethylene glycol tags used in studies of the present invention.

The sorting tags of the present invention are, for example, useful in any type of application wherein a number of molecules are to be processed simultaneously and then separated. This is of particular interest, for example, to those involved in drug discovery and materials science. FIGS. 1A and 1B illustrate two such applications. In FIG. 1A, 8 starting materials or compounds $R_n$, each tagged with a sorting tag $T_n$ of a different length (that is, having a different number of repeat units) such as oligoethylene glycols (OEGs) of different length, are combined in a single flask and transformed into products $T_nR'_n$. The presence of the OEG tags, when coupled with the complementary chromatographic separation method, allows the eight products to be separated in one chromatography. In FIG. 1B, 4 tagged starting materials $R_nT_n$ are combined in one flask and coupled with a mixture of 4 other tagged materials $R_mT_m$. The first and second sets of molecules are labeled with different sorting tags ($T_n$ and $T_m$, respectively). For example, 4 OEGs can be used for the starting materials and 4 alternative tags (for example, fluorous tags) can be used for a second set reactants that are to be attached to the starting materials. The resultant 16 coupled products can be separated in predictable order in, for example, just two chromatographic runs (see FIG. 1B). Such a separation can alternatively occur in a 2-dimensional preparative plate chromatogram. In that regard, FIG. 2 illustrates a spatial separation of all 16 products (represented by concentric circles) in a 2-dimensional preparative plate chromatogram.

The oligomeric (and other repeating unit) sorting tags of the present invention provide a general solution to the problem of sorting a mixture of organic compounds into its constituent parts. The oligomeric/repeating unit design of the tags of the present invention together with the great number of possible oligomers available makes possible a broad range of sorting tags that may be designed for use with any class of compounds. Although the representative examples of the present invention set forth below demonstrate the present invention using OEGs, there are many other readily available oligomers suitable for use as sorting tags. The chromatography stationary phases required for separation of OEG sorting tags and other polar sorting tags of the present invention are commercially available. Moreover, many of the OEGs and other sorting tags of the present invention are bulk commodities and the ultimate price of tags can be low. The OEG-tagged and other tagged molecules (as well as the sorting tags) can be separated using common solvents used in the chemical processing industry.

Preferred solid or stationary phases for use in the present invention for separations complementary to the polar tags of the present invention are polar and are selected from an array of common chromatographic stationary phases. Many porous or mesoporous inorganic oxides or polymers, or bonded phases thereof, are useful. Examples of typical solid phases include silica gel (sold in many forms under many names), alumina (sometimes called aluminum oxide), titania, or zirconia. Polar bonded phases of silica gel and related media are also useful. Such bonded phases include a plethora of polar groups including, for example, hydroxy groups, amino groups, ammonium groups, sulfonate groups, carboxylate groups and nitrile groups. Other stationary phases suitable for use in the present invention include non-polar bonded phases of silica gel such as reverse phase silica gel with a hydrocarbon bonded phase.

Figure 3:
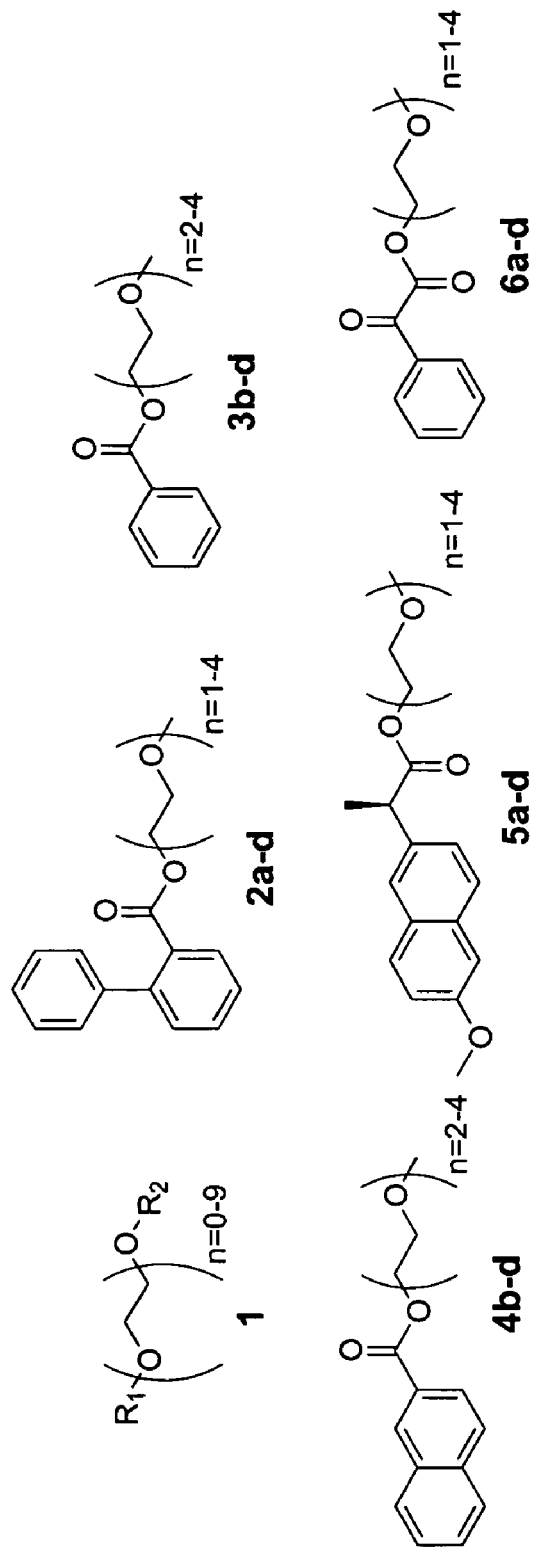
FIG. 3 illustrates an number of esters tagged with tagging moieties of the present invention.

As illustrated in FIG. 3, several studies of the present invention focused on OEG derivatives (1) that contain five or fewer ethylene glycol repeat units. OEG derivatives (sometimes referred to as "lariat ethers") are known to form complexes with group IA cations such as $Li^+$, $Na^+$, and $K^+$. The magnitudes of the formation constants ($K_f$) for these complexes differ with the length of the OEG unit. Gokel, G. W.; Dishong, D. M.; Diamond, C. J. *Chem. Comm.*, 1980, 22, 1053-4; Chan, L. L.; Wong, K. H.; Smid, J., *J. Am. Chem. Soc.*, 1970, 92, 1955-1963. Initially, it was hypothesized that OEG tags might work well as sorting tags on chromatography columns doped with group IA cations. Surprisingly, it was discovered that such OEG tags differed sufficiently in polarity to work well as sorting tags in standard chromatographic columns without doping. However, addition of additives including group IA cations can improve separation in certain circumstances.

Esters 2a-6d were prepared via conventional methods from commercially available starting materials. A mixture containing 18 esters was prepared and separation was tested on several chromatographic columns. In a single pass on a normal silica column (5μ Supelcosil), 17 of the 18 esters were separated (see FIG. 4) Identification of individual peaks was accomplished by comparing the retention times of pure compounds to the retention times of components in the mixture and by analyzing the UV-VIS spectra of the component peaks.

As illustrated in FIG. 4, the esters separated into 4 major subregions based on the length of the OEG moiety. The subregions include five peaks wherein n is 4, five peaks wherein n is 3, four peaks wherein n is 2 and four peaks wherein n is 1. Within each subregion, the separation was dependent on the structure of the acid component portion. The elution order was conserved within each subregion (2-3-4-5-6). Similar chromatograms (not shown) were obtained on another silica column (10μ VersaPak) and on a cyclodextrin column (5μ Cyclobond I).

The effect upon retention times of the OEG tagged molecules upon addition of group IA cations to the chromatography medium was also studied. In these studies, a number of TLC plates were prepared by immersing standard analytical silica plates in aqueous solutions of different group IA salts and then drying the plates at 150° C.

Figure 5:
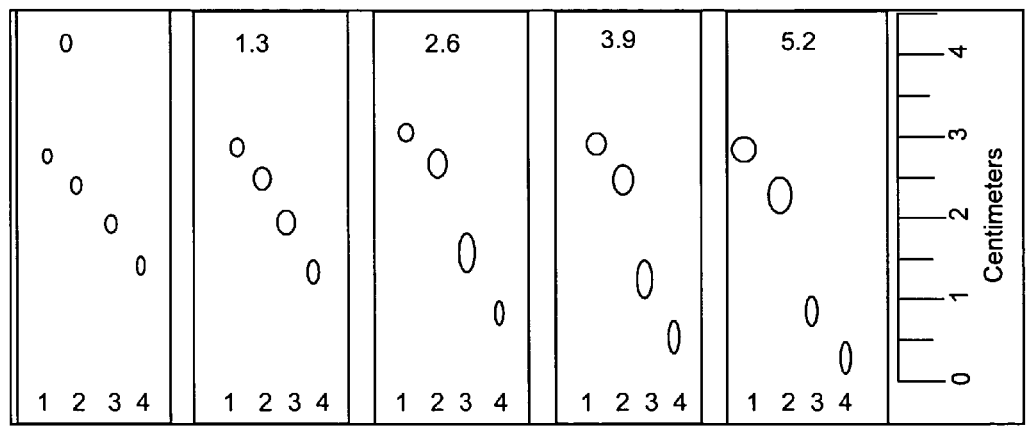
FIG. 5 illustrates TLC results for esters 5a-d of FIG. 4, wherein the TLC plates were immersed 0, 1.3, 2.6, 3.9, and 5.2 M aqueous LiCl (respectively, from left to right) and then dried prior to development with EtOAc.

The $R_f$ values for 5a-d on these treated and untreated TLC plates and with a number of eluents are set forth in Table 1 below. $R_f$ is the chromatographic retention factor. In that regard, the retention factor $R_f$ of a compound in TLC is defined as the distance traveled by the compound divided by the distance traveled by the solvent front. The retention factor $R_f$ should not be confused with the chemical substituent designation $R_F$, discussed below, which represents a fluorous moiety or group. It was found that improved separation was obtained for a $8.73 \times 10^{-5}$ mol/cm$^2$ concentration of Li$^+$ (entries 1-6) as a result of the retarding effect of the salt additive. The retarding effect is larger for the longer OEGs 5c,d than for the shorter tagged esters 5a,b. The comparatively reduced effect of Na$^+$ and K$^+$ salts (entry 6-7) agrees with the known $K_f$ values for OEG/Li$^+$ and OEG/Na$^+$ complexes. Both DME and THF caused the esters to elute closer to each other (entries 9-14). TLC results for esters 5a-d with TLC plates immersed in 0, 1.3, 2.6, 3.9, and 5.2 M aqueous LiCl (respectively, from left to right) and then dried prior to development with EtOAc are illustrated in FIG. 5. The best separation is exhibited with the 5.2M aqueous LiCl plast (far right in FIG. 5).

TABLE 1

Separation of 5a-d by TLC under various conditions

| Entry | [M$^+$] (mol/cm$^2$)$^a$ | 5a$^{b,h}$ | 5b$^{b,h}$ | 5c$^{b,h}$ | 5d$^{b,h}$ | Eluent |
|---|---|---|---|---|---|---|
| (1) | 0 | 0.70 | 0.60 | 0.46 | 0.34 | EtOAc |
| (2) | 1.72 × 10$^{-5}$ (Li$^+$) | 0.75 | 0.64 | 0.33 | 0.18 | EtOAc |
| (3) | 3.73 × 10$^{-5}$ (Li$^+$) | 0.76 | 0.63 | 0.34 | 0.19 | EtOAc |
| (4) | 6.63 × 10$^{-5}$ (Li$^+$) | 0.70 | 0.6 | 0.34 | 0.16 | EtOAc |
| (5) | 8.73 × 10$^{-5}$ (Li+) | 0.71 | 0.59 | 0.22 | 0.11 | EtOAc |
| (6) | 1.09 × 10$^{-4}$ (Li+) | 0.70 | 0.59 | 0.22 | 0.10 | EtOAc |
| (7) | 8.9 × 10$^{-5}$ (Na$^+$) | 0.75 | 0.63 | 0.48 | 0.38 | EtOAc |
| (8) | 6.1 × 10$^{-5}$ (K$^+$) | 0.78 | 0.68 | 0.53 | 0.33 | EtOAc |
| (9) | 0 | 0.50 | 0.29 | 0.15 | 0.08 | $c$ |
| (10) | 8.73 × 10$^{-5}$ (Li$^+$) | 0.56 | 0.34 | 0.08 | 0.03 | $c$ |
| (11) | 8.73 × 10$^{-5}$ (Li$^+$) | 0.59 | 0.48 | 0.30 | 0.20 | $d$ |
| (12) | 8.73 × 10$^{-5}$ (Li$^+$) | 0.78 | 0.75 | 0.68 | 0.62 | DME |
| (13) | 8.73 × 10$^{-5}$ (Li$^+$) | 0.58 | 0.45 | 0.23 | 0.11 | $e$ |
| (14) | 8.73 × 10$^{-5}$ (Li$^+$) | 0.64 | 0.58 | 0.50 | 0.39 | THF |
| (15) | 0 | 0.73 | 0.65 | 0.51 | 0.38 | $f$ |
| (16) | 0 | 0.75 | 0.64 | 0.61 | 0.58 | $g$ |
| (17) | 3.73 × 10$^{-5}$ (Li$^+$) | 0.78 | 0.65 | 0.43 | 0.30 | $g$ |

$^a$Concentration of metal ions on the surface of the TLC plate.
$^b$$R_f$ values.
$^c$1:1 EtOAc:Hex.
$^d$1:1 DME:Hex.
$^e$1:1 THF:Hex.
$^f$0.1M LiClO$_4$ in EtOAc.
$^g$1M LiClO$_4$ in EtOAc.
$^h$Variation in $R_f$ values was ± 0.05.

Without being limited to any specific mechanism of operation, a working hypothesis to explain the above observations includes (a) direct binding of the OEG tags to silica, (b) binding of OEGs to amorphous or crystalline clusters of Li$^+$, solubilization of lithium salts by the OEGs, and binding of OEGs to surface ion clusters (c) and single ions (d). To evaluate the retention behavior of the solvated [OEG . . . Li$^+$] complex, a soluble lithium salt (LiClO$_4$) was added to the eluent (Table 1, entries 13-15) in a control experiment. At 1 M LiClO$_4$ in EtOAc, on untreated silica plates, a leveling effect was observed. The $R_f$ values of the longer OEGs were increased. This would be expected if the solvated lithium ion competitively displaces the OEG from the silica surface and the [OEG . . . Li$^+$] complex has higher mobility than the OEG alone. The leveling effect of LiClO$_4$ is also present, though less pronounced, on plates treated with LiCl. (Table 1, entries 15-17).

The above studies clearly indicate that OEG derivatives can be useful sorting tags for chromatography either with or without dopants. OEG derivatives are inexpensive and separations using OEG tags can be achieved with standard laboratory equipment (for, example HPLC and flash columns were used in the present studies) on regular silica media. The OEG and other tags of the present invention can also be used together with other types of tags to, for example, further the scope of mixture synthesis.

Figure 6:
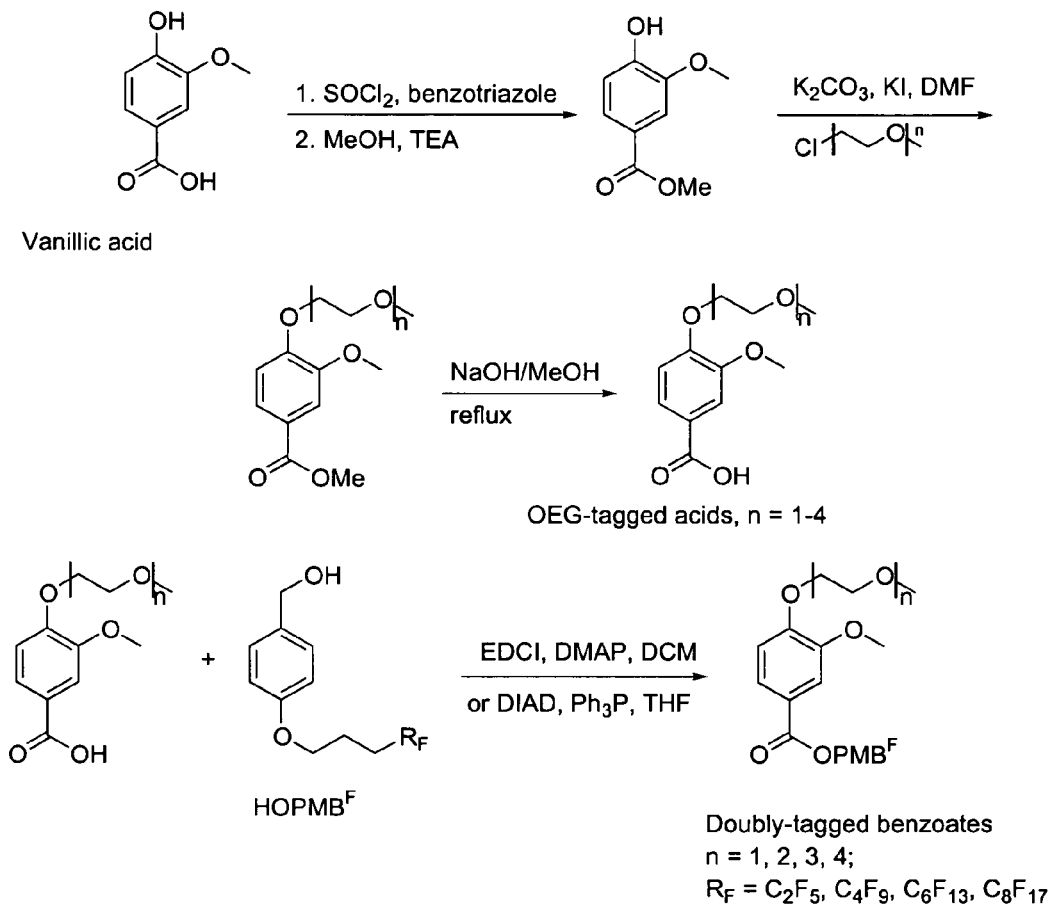
FIG. 6 illustrates the synthesis of sixteen analogs of 4-hydroxy-3-methoxybenzoic acid tagged with oligoethylene tags and with fluorous tags.

In one study of double tagging with OEG tags and fluorous tags, a mixture of sixteen doubly tagged analogs of vanillic acid (4-hydroxy-3-methoxybenzoic acid) was created wherein each compound had one of a series of four OEG tags on the phenolic hydroxy group and one of a series of four fluorous tags on the carboxylate group. The resulting sixteen compounds (4×4) are each uniquely encoded by the combination of the OEG tag and the fluorous tag. This sixteen-compound mixture was synthesized as shown in FIG. 6. Four individual OEG-tagged acids (n=1-4) were prepared by standard reactions and then mixed. The resulting mixture was coupled with a mixture of four fluorous alcohols HOPMB$^F$ (including perfluoroalkyl R$_F$ groups of differing length/fluorine content) as indicated in FIG. 67 under standard Mitsunobu conditions to provide the sixteen compound mixture.

The sixteen compound mixture was demixed into sixteen individual components based on the tags by a series of two demixings, one targeted to each class or type of tag. TLC analysis of the mixture on standard silica gel (see FIG. 7 at the top thereof) showed four spots. The mixture was separated into four fractions by standard flash chromatography (pentane/ethyl acetate gradient elution), and analysis of the fractions in order of decreasing polarity showed the following results: Fraction 1 (least polar) contained all four fluorous-tagged compounds bearing OEG1 (n=3), Fraction 2 contained all four fluorous-tagged compounds bearing OEG2 (n=2), Fraction 3 contained all four fluorous-tagged compounds bearing OEG3 (n=3), and Fraction 4 (most polar) contained all four fluorous-tagged compounds bearing OEG4 (n=4). Each of these four fractions was further demixed by standard fluorous chromatography on a FLUOROFLASH hplc column. As expected, the products in this chromatography eluted in order of fluorous tag from C$_2$F$_5$ up to C$_8$F$_{17}$. This provided all 16 individual products.

The order of the demixings can also be reversed, with the fluorous demixing being conducted before the OEG demixings. FIG. 7 (at the bottom thereof) shows an analytical hplc trace of the 16 compound mixture on a FluoroFlash PF-C8 column. The compounds emerged as four groups of four peaks. The larger separations corresponded to the fluorous tag, with the four compounds bearing the C$_2$F$_5$ tag eluting well before the four compounds bearing the C$_4$F$_9$ tag, etc. The smaller separations within the groups of peaks correspond to OEG separation from the more polar n=4 tag to the less polar n=1 tag. The mixture was separated by semi-preparative hplc on the PF-C8 column. In this case, only four fractions corresponding to the four different groups of fluorous-tagged compounds were collected. Each of these fractions containing four molecules with one fluorous tag and all four OEG tags were then separated by flash chromatography as above to provide the same sixteen individual products.

In this manner, all sixteen individual pure products were isolated in predictable fashion from the sixteen compound mixture with only five chromatographies. Only eight tags were needed to encode all sixteen compounds. The ability to conduct the double demixing in one of two possible orders adds further flexibility to the method.

FIGS. 6 and 7 illustrate the potential for use of a dual or "chimeric" tag of the present invention. In that regard, two or more types of tags can be added to each of several compounds via a common group or atom, for later separation using, for example, two different types of chromatographic separation techniques. For example, an OEG tag and a fluorous tag ($R_F$) can be attached to a common spacing or connecting compound or group D as illustrated below:

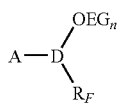

In the above structure, A represents a reactive functional group through which the chimeric tag can be attached to a compound to synthesize a doubly tagged compound. Alternatively, two or more types of tag can be connected to each other as illustrated below

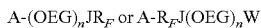

In the above structure, A once again represents a reactive functional group through which the chimeric tag can be attached to a compound. J is a connecting group (for example —O—), which may or may not be present. W is and end group (for example, a methyl group). Use of chimeric tags can, for example, be advantageous (or even necessary) in the case that a group of compounds to be tagged includes only a single functional atom or group through which tagging can occur. Representative examples of fluorous/OEG chimeric tags include, but are not limited to, $HOCH_2C_6H_3$-3-(($OCH_2CH_2)_NOCH_3$)-4-($OCH_2CH_2R_F$), $HO(CH_2CH_2O)_nCH_2CH_2R_F$ and $HOCH_2CH_2—R_F—CH_2CH_2(OCH_2CH_2)_nOCH_3$.

In a further study, a mixture synthesis of stereoisomers of murisolin was first performed by applying fluorous mixture synthesis where a 4-compound mixture/4-split strategy was employed to synthesize and separate 16 different stereoisomers of murisolin. In that regard, four different fluorous tags were used in connection with four different reaction mixtures. A separate fluorous separation was then performed for each of the four different reaction mixtures. In a further study of the present invention, the fluorous mixture synthesis was advanced to a single, 16-compound mixture strategy using four OEG tags of the present invention in combination with the four fluorous tags used in the initial studies. A significant volume of eluent is saved by using a 16-compound mixture strategy rather that using a 4-compound mixture/4-split strategy or sixteen individual compounds.

Figure 9:
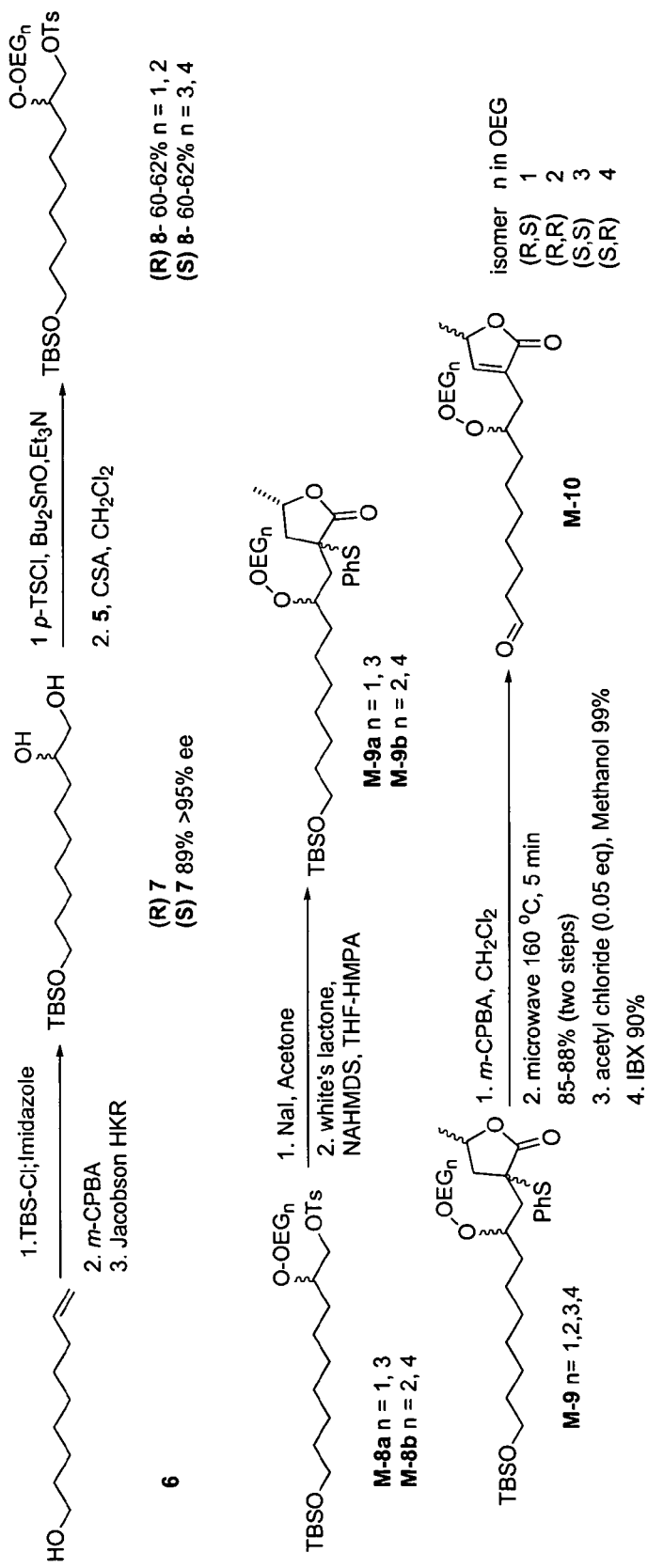
FIG. 9 illustrates a mixture synthesis of oligoethylene glycol tagged stereoisomers of murisolin.
Figure 10:
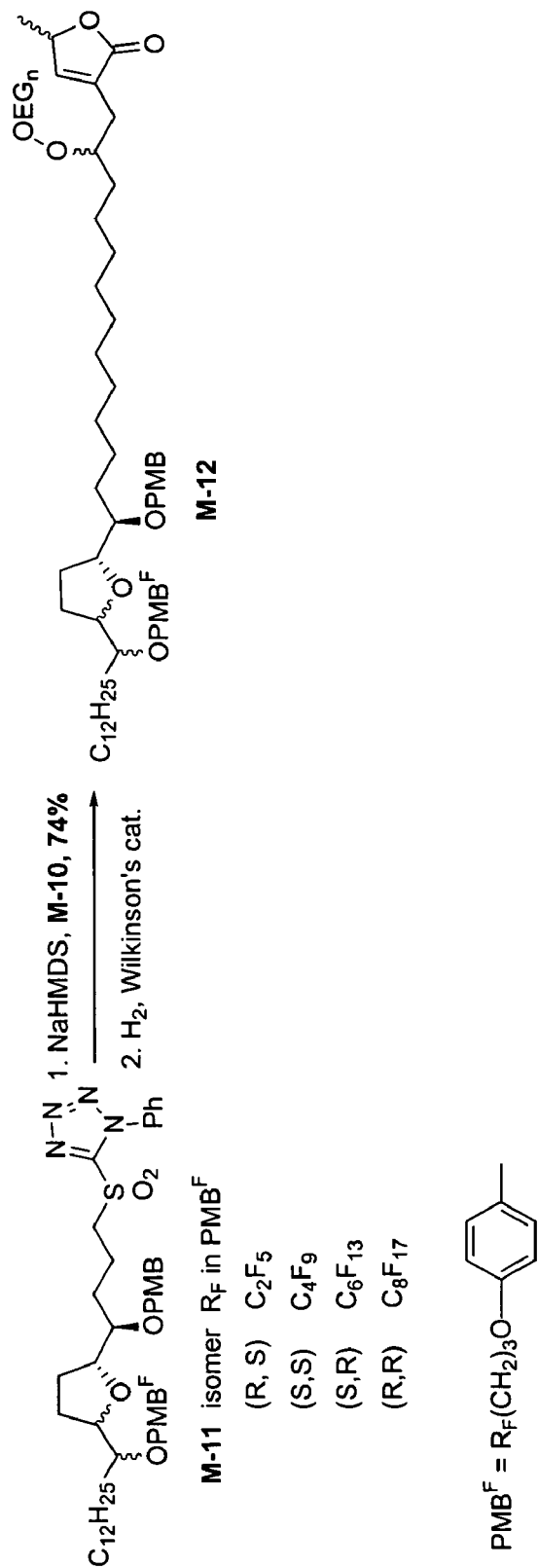
FIG. 10 illustrates fluorous tagging of the oligoethylene glycol tagged stereoisomers of murisolin.

As illustrated in FIG. 8, OEG tags were synthesized from vanillic acid 3 (4-hydroxy-3-methoxy benzoic acid). As described generally above, the different OEG tags 4 and 5 had homologous poly-ethyleneglycol chains which imparted different polarity to the molecules against regular silica or TLC chromatography. The higher the number of ethyleneglycol units in an OEG tag, the greater was its polarity. The remarkable difference in polarity of OEG tags allowed the mixture synthesis of isomers by facilitating predictable separation during purification and demixing. The OEG-mixture synthesis strategy was applied to the synthesis of four compound mixture M-10 as illustrated in FIG. 9. In FIGS. 9 and 10, the prefix "M" denotes a mixture.

As illustrated in FIG. 9, TBS protection, epoxidation followed by Jacobson hydrolytic kinetic resolution provided (R)-7, (S)-7 in >95% enantiomeric excess (ee). Mono-tosylation of 7 followed by tethering the secondary alcohol with OEG tags resulted in 8, the starting point for the OEG mixture synthesis. Mixtures M-8a and M-8b were individually subjected to Finkelstein reaction followed by alkylation with S, R White's lactone respectively. See Schaus, S. E.; Brandes, B. D.; Larrow, J. F.; Tokunaga, M.; Hansen, K. B.; Gould, A. E.; Furrow, M. E.; Jacobson, E. N. *J. Am. Chem. Soc.* 2002, 124, 1307; Martinelli, M. J.; Naayaar, N. K.; Moher, E. D. L Dhokte, U. P.; Pawlak, J. W.; Vaidyanathan, R. *Org. Lett*, 1999, 1, 447; White, J. D.; Somers, T. C.; Reddy, G. N. *J. Org. Chem.* 1992, 57, 4991; Schaus, S. E.; Brånalt, B.; Jacobsen, E. N. *J. Org. Chem.* 1998, 63, 4876. The resulting M-9a and M-9b were mixed to yield four component mixture M-9 which was subjected to oxidation, elimination, deprotection and oxidation to give M-10.

Figure 11:
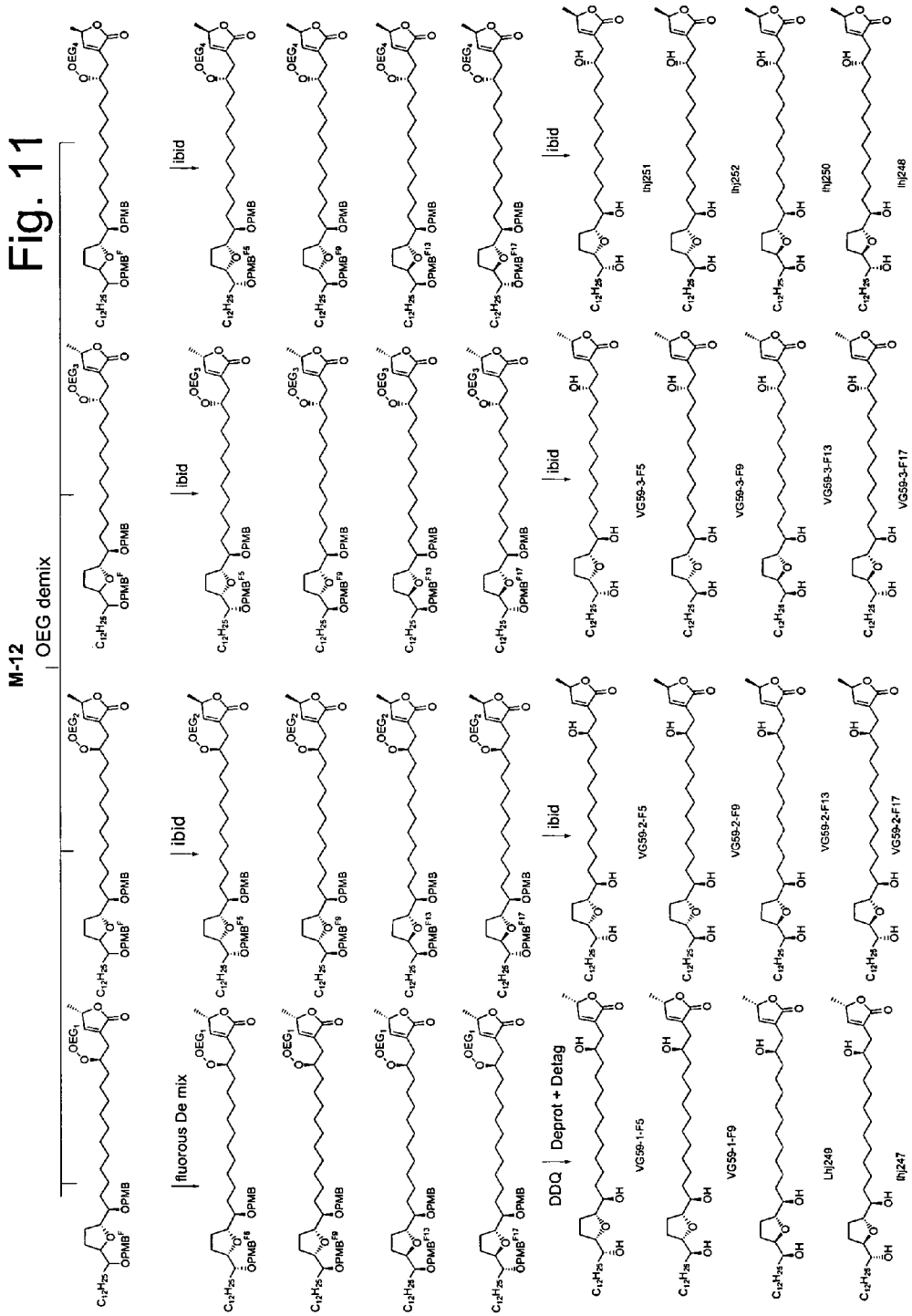
FIG. 11 illustrates separation of the tagged stereoisomers of murisolin via OEG demixing followed by fluorous demixing and subsequent detagging.

Sixteen compound mixture M-12 was obtained by Julia-Kocienski coupling of M-10 with M-11 followed by Wilkinson's reduction as illustrated in FIG. 10. M-11 is a mixture of four stereoisomers having configurations encoded by fluorous tags $PMB^F$ which are fluorous analogs of paramethoxy benzyl groups. In postmix stage as illustrated in FIG. 11, demixing of M-12 by regular silica-flash chromatography resulted in four mixtures—M-13-OEG1, M-13-OEG2, M-13-OEG3 and M-13-OEG4. Each of the M-13 mix was individually subjected to fluorous separation (fluorous-prep-HPLC) to yield four components. The resultant sixteen tagged murisolin isomers were individually subjected to detagging and further purifications to yield isomerically pure murisolin isomers.

As seen from the above examples, combination of more than one type of tag (for example, combination of non-fluorous, OEG or other polar repeat unit tags of the present invention and available fluorous tags) results in a powerful encoding/tagging and separation tool with use of only a moderate number of tags of each type. In that regard, use of an amount "a" of tags of type 1 and an amount "b" of tags of type 2, enables separation of a mixture of a×b tagged compounds. Use of only one type of tag (for example, an OEG tag or a fluorous tag) to separate the mixture of compounds would require a×b different tags of that type. While the murisolin isomer synthesis described above illustrates the encoding and separation of stereoisomers, it is also possible to encode/separate analogs having different structures.

EXPERIMENTAL EXAMPLE

Example 1

Double Demixings of the 16 Compound Mixture of Fluorous and OEG Tagged 4-hydroxy-3-Methoxybenzoates Method 1: One silica flash column followed by four fluorous prep-HPLCs: The mixture was first separated via flash column chromatography on silica gel with gradient eluents (pentane/ethyl acetate 5:1, 3:1, 2:1, 1:1, 1:2 and 1:4) to give four fractions according to the OEG tags (each of the fractions contained four compounds with different fluorous tags). Each of the fractions was then dissolved in 1.5 mL of $CH_3CN$ and injected onto a FluoroFlash PF-C8 hplc column (20×250 mm). The column was eluted under a linear gradient conditions. The gradient started with 60% $CH_3CN$/40% $H_2O$ and ended with 100% $CH_3CN$ in 30 min. The flow rate was 15 mL/min. The four fractions in each injection with retention time of ~7 min, ~12 min, ~19 min and ~23 min were collected separately and concentrated to give the sixteen individual compounds respectively.

Method 2. One fluorous prep-HPLC followed by four silica flash columns: The mixture was dissolved in $CH_3CN$. About 1.5 mL of this solution was injected onto a FluoroFlash PF-C8 column (20×250 mm) each time. The column was eluted under a linear gradient condition for 30 min. The gradient started with 60% $CH_3CN$/40% $H_2O$ and ended with 100% $CH_3CN$ in 30 min. The flow rate was 15 mL/min. The four fractions with retention time of ~7 min, ~12 min, ~19 min and ~23 min were collected separately and concentrated. Each of the fractions contained four compounds with one fluorous tag and all four different OEG tags. These fractions were then separated via flash column chromatography on silica gel with gradient eluents (pentane/ethyl acetate 5:1, 3:1, 2:1, 1:1, 1:2 and 1:4) to give the individual compounds.

Example 2

Encoded Synthesis and Separation of Sixteen Stereoisomers of Murisolin. Julia Olefination and Hydrogenation A solution of the sulfone M-11 in THF was cooled to −78° C. and NaHMDS was added under argon. The reaction mixture was stirred at −78° C. for 30 min and a solution of the aldehyde M-11 in THF was then transferred in via cannula. The resulting mixture was then warmed to room temperature overnight and $H_2O$ was added. The layers were separated and the aqueous layer was further extracted with $Et_2O$ (3×20 mL). The combined organic layers were washed with brine, dried over $MgSO_4$ and concentrated under vacuum. The residue was purified by gradient flash chromatography (pentane/ethyl acetate 10:1, 5:1, 2:1 and then pure ethyl acetate) on silica gel to yield the coupling products as four components (as according to the OEG tags).

LCMS (APCI): a m/z: 1159 $(M_1+1)^+$, 1176 $(M_1+H_2O)^+$, 1203 $(M_2+1)^+$, 1220 $(M_2+H_2O)^+$, 1264 $(M_3+H_2O)^+$, 1308 $(M_4+H_2O)^+$; b m/z: 1259 $(M_1+1)^+$, 1276 $(M_1+H_2O)^+$, 1303 $(M_2+1)^+$, 1320 $(M_2+H_2O)^+$, 1347 $(M_3+1)^+$, 1364 $(M_3+H_2O)^+$, 1391 $(M_4+1)^+$, 1408 $(M_4+H_2O)^+$, 367 $[C_4F_9(CH_2)_3OC_6H_4CH_2]^+$; c m/z: 1376 $(M_1+H_2O)^+$, 1403 $(M_2+1)^+$, 1420 $(M_2+H_2O)^+$, 1447 $(M_3+1)^+$, 1464 $(M_3+H_2O)^+$, 1491 $(M_4+1)^+$, 1508 $(M_4+H_2O)^+$, 467 $[C_6F_{13}(CH_2)_3 OC_6H_4CH_2]^+$; d m/z: 1459 $(M_1+1)^+$, 1476 $(M_1+H_2O)^+$, 1520 $(M_2+H_2O)^+$, 1564 $(M_3+H_2O)^+$, 1608 $(M_4+H_2O)^+$, 1444 $[M_1-CH_3O]^+$, 1488 $[M_2-CH_3O]^+$, 567 $[C_8F_{17}(CH_2)_3 OC_6H_4CH_2]^+$.

The four fractions were then mixed together and taken up in EtOH. Wilkinson's catalyst (10-15%) was then added. The resulting mixture was stirred under $H_2$ atmosphere (1 atm) and followed by $^1H$ NMR spectroscopy until the reaction completed. The reaction mixture was then concentrated under vacuum to give the crude final product mixture M-12.

Demixing of Final 16-Compound Mixture M-12:

OEG demixing: Purification and OEG demixing of the final mixture was done simultaneously by a careful flash column chromatography on silica gel. Gradient eluent was used as hexane/ethyl acetate 10:1, 5:1, 2:1 and then pure ethyl acetate. Four fractions were obtained as according to the OEG tags.

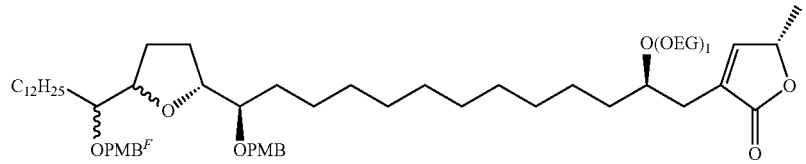

LCMS (APCI) for a m/z: 1178 $(M+H_2O)^+$, 965, 581, 267 $[C_2F_5(CH_2)_3OC_6H_4CH_2]^+$; b m/z: 1278 $(M+H_2O)^+$, 1139 $(M-PMB)^+$, 581, 367 $[C_4F_9(CH_2)_3OC_6H_4CH_2]^+$; c m/z: 1378 $(M+H_2O)^+$, 1239 $(M-PMB)^+$, 581, 467 $[C_6F_{13}(CH_2)_3 OC_6H_4CH_2]^+$; d m/z: 1478 $(M+H_2O)^+$, 581, 567 $[C_8F_{17}(CH_2)_3OC_6H_4CH_2]^+$.

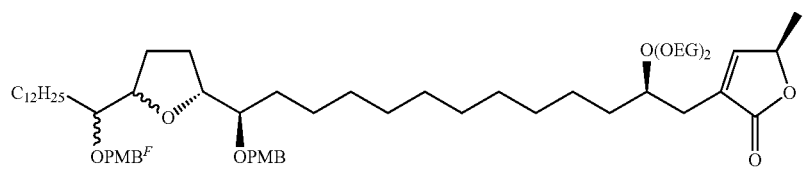

LCMS (APCI) for a m/z: 1222 $(M+H_2O)^+$, 581, 561, 267 $[C_2F_5(CH_2)_3OC_6H_4CH_2]^+$; b m/z: 1322 $(M+H_2O)^+$, 581, 561, 367 $[C_4F_9(CH_2)_3OC_6H_4CH_2]^+$; c m/z: 1422 $(M+H_2O)^+$, 581, 561, 467 $[C_6F_{13}(CH_2)_3OC_6H_4CH_2]^+$; d m/z: 1522 $(M+H_2O)^+$, 581, 567 $[C_8F_{17}(CH_2)_3OC_6H_4CH_2]^+$.

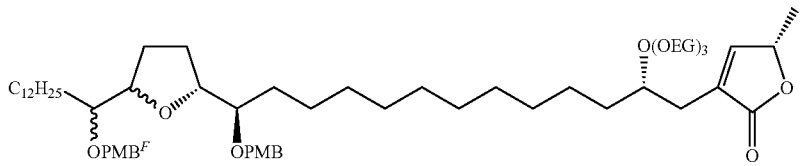

LCMS (APCI) for a m/z: 1266 (M+H$_2$O)$^+$, 581, 561, 267 [C$_2$F$_5$(CH$_2$)$_3$OC$_6$H$_4$CH$_2$]$^+$; b m/z: 1366 (M+H$_2$O)$^+$, 581, 561, 403, 367 [C$_4$F$_9$(CH$_2$)$_3$OC$_6$H$_4$CH$_2$]$^+$; c m/z: 1466 (M+H$_2$O)$^+$, 581, 561, 467 [C$_6$F$_{13}$(CH$_2$)$_3$OC$_6$H$_4$CH$_2$]$^+$; d m/z: 1566 (M+H$_2$O)$^+$, 581, 567 [C$_8$F$_{17}$(CH$_2$)$_3$OC$_6$H$_4$CH$_2$]$^+$.

$^1$H NMR (600 MHz, CDCl$_3$) δ 0.03 (s, 3H), 0.06 (s, 3H), 0.07 (s, 3H), 0.09 (s, 3H), 0.87-0.90 (m, 3H), 0.88 (s, 9H), 0.90 (s, 9H), 1.26-1.36 (m, 36H), 1.42-1.46 (m, 4H), 1.42 (d, J=6.8 Hz, 3H), 1.50-1.53 (m, 2H), 1.62-1.66 (m, 1H), 1.76-

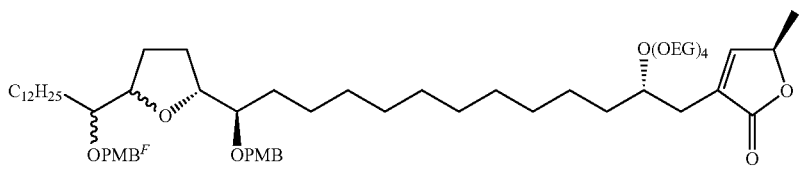

10

LCMS (APCI) for a m/z: 1310 (M+H$_2$O)$^+$, 279; b m/z: 1410 (M+H$_2$O)$^+$, 279; c m/z: 1510 (M+H$_2$O)$^+$, 279; d m/z: 1610 (M+H$_2$O)$^+$, 279.

Fluorous demixing: Each of the four mixtures was dissolved in CH$_3$CN. About 1.5 mL of this solution was injected onto a Fluoroflash column (20×250 mm) each time. The column was eluted under a linear gradient followed by isocratic conditions for 35 min. The gradient started with 85% CH$_3$CN/15% H$_2$O and ended with 100% CH$_3$CN in 25 min. The isocratic solvent 100% CH$_3$CN was eluted for 10 min. The flow rates in both are 15 mL/min. Four fractions with retention time of ~10 min, ~15 min, ~19 min and ~23 min were collected separately and concentrated to give the individual fluorous-OEG double-tagged products respectively. Sample data of four dimixing products (from the OEG-1 fraction):

1.80 (m, 1H), 1.82-1.87 (m, 2H), 2.06-2.12 (m, 2H), 2.23-2.31 (m, 2H), 2.43 (d, J=5.6 Hz, 2H), 3.46 (q, J=6.1 Hz, 1H), 3.66 (q, J=6.4 Hz, 1H), 3.78 (q, J=7.9 Hz, 1H), 3.85 (q, J=4.9 Hz, 1H), 3.96 (quintet, J=5.7 Hz, 1H), 4.03 (t, J=5.9 Hz, 2H), 4.52 (d, J=11.2 Hz, 1H), 4.60 (d, J=11.2 Hz, 1H), 5.01 (q, J=6.9 Hz, 1H), 6.86 (d, J=8.5 Hz, 2H), 7.13 (s, 1H), 7.27 (d, J=8.5 Hz, 2H); $^{19}$F NMR (282.4 MHz, CDCl$_3$) δ −117.1 (2F), −84.3 (3F); $^{13}$C NMR (151.1 MHz, CDCl$_3$) δ −4.50, −4.37 (2C), −4.08, 14.19, 18.13, 18.34, 19.05, 20.80, 22.77, 25.24, 25.42, 25.63, 25.96, 26.07, 26.77, 26.78, 27.78 (t, J$_{FC}$=22.2 Hz), 29.45, 29.69, 29.72, 29.74, 29.76, 29.79, 29.82, 29.90, 29.98, 31.85, 32.01, 32.82, 33.10, 37.07, 66.41, 70.28, 72.38,

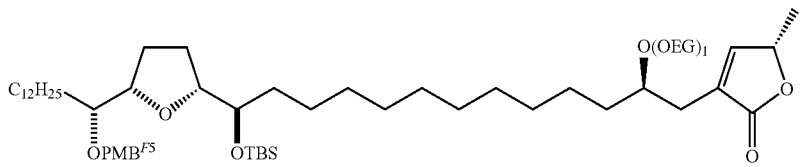

74.62, 77.53, 80.25, 81.62, 82.43, 105.5-124.0 (m, C$_2$F$_5$), 114.33, 129.41, 130.97, 131.90, 151.53, 158.07, 174.11; CIMS m/z: 1092.7 (M+H$_2$O)$^+$, 807.7, 675.5, 543.3, 267.0.

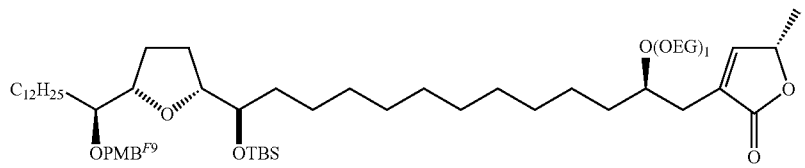

$^1$H NMR (300 MHz, CDCl$_3$) δ 0.03 (s, 3H), 0.06 (s, 3H), 0.07 (s, 3H), 0.08 (s, 3H), 0.87-0.91 (m, 3H), 0.88 (s, 9H), 0.90 (s, 9H), 1.20-1.38 (m, 36H), 1.40-1.48 (m, 4H), 1.42 (d, J=6.8 Hz, 3H), 1.49-1.62 (m, 3H), 1.63-1.86 (m, 3H), 2.02-2.18 (m, 2H), 2.21-2.40 (m, 2H), 2.43 (d, J=5.6 Hz, 2H), 3.31-3.40 (m, 1H), 3.65 (q, J=4.7 Hz, 1H), 3.84-3.98 (m, 3H), 4.03 (t, J=5.9 Hz, 2H), 4.53 (d, J=11.3 Hz, 1H), 4.71 (d, J=11.3 Hz, 1H), 5.01 (qd, J=6.8 Hz, 1.5 Hz, 1H), 6.86 (d, J=8.7 Hz, 2H), 7.12 (d, J=1.4 Hz, 1H), 7.29 (d, J=8.6 Hz, 2H); $^{19}$F NMR (282.4 MHz, CDCl$_3$) δ −124.8 (2F), −123.2 (2F), −113.4 (2F), −79.8 (3F); $^{13}$C NMR (75 MHz, CDCl$_3$) δ −4.4, −4.3 (2C), −4.1, 14.2, 18.2, 18.3, 19.1, 20.8, 22.8, 25.3, 25.8, 26.0, 26.1, 26.9, 28.0, 28.1 (t, J$_{FC}$=22.4 Hz), 29.5, 29.6-30.0 (m), 30.1, 31.1, 32.1, 32.9, 33.1, 37.1, 66.5, 70.3, 72.5, 74.6, 77.6, 81.4, 81.8, 82.3, 105.8-120.0 (m, C$_4$F$_9$), 114.3, 129.7, 131.0, 132.1, 151.6, 158.1, 174.1; CIMS m/z: 1192.7 (M+H$_2$O)$^+$, 1173.7, 807.7, 675.5, 543.3, 367.0.

$^1$H NMR (300 MHz, CDCl$_3$) δ 0.03 (s, 3H), 0.06 (s, 3H), 0.07 (s, 3H), 0.08 (s, 3H), 0.87-0.96 (m, 3H), 0.88 (s, 9H), 0.89 (s, 9H), 1.21-1.37 (m, 36H), 1.37-1.54 (m, 5H), 1.42 (d, J=6.8 Hz, 3H), 1.55-1.70 (m, 3H), 1.78-1.94 (m, 2H), 2.02-2.16 (m, 2H), 2.20-2.38 (m, 2H), 2.43 (d, J=5.4 Hz, 2H), 3.30 (q, J=5.4 Hz, 1H), 3.55-3.66 (m, 1H), 3.90-4.01 (m, 3H), 4.04 (t, J=5.8 Hz, 2H), 4.53 (d, J=11.3 Hz, 1H), 4.67 (d, J=11.3 Hz, 1H), 5.02 (q, J=6.6 Hz, 1H), 6.85 (d, J=8.1 Hz, 2H), 7.12 (s, 1H), 7.28 (d, J=8.1 Hz, 2H); $^{19}$F NMR (282.4 MHz, CDCl$_3$) δ −124.9 (2F), −122.2 (2F), −121.5 (2F), −120.7--120.5 (m, 6F), −1132.2 (2F), −79.6 (3F); $^{13}$C NMR (75 MHz, CDCl$_3$) δ −4.5, −4.3 (2C), −4.2, 14.1, 18.0, 18.2, 19.0, 22.7, 25.1, 25.6, 25.8, 26.0, 27.5, 28.0 (t, J$_{FC}$=22.4 Hz), 29.4, 29.6, 29.9, 30.8, 31.9, 32.7, 33.0, 37.0, 66.3, 70.1, 72.1, 75.0, 81.0, 81.6 (2C), 81.8, 105.0-120.4 (m, C$_8$F$_{17}$), 114.1, 129.5, 130.8, 131.9, 151.5, 157.9, 174.0.

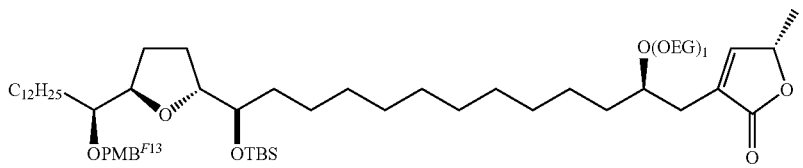

$^1$H NMR (300 MHz, CDCl$_3$) δ 0.03 (s, 3H), 0.06 (s, 3H), 0.07 (s, 3H), 0.10 (s, 3H), 0.87-0.99 (m, 3H), 0.88 (s, 9H), 0.90 (s, 9H), 1.20-1.38 (m, 36H), 1.37-1.54 (m, 5H), 1.42 (d, J=6.8 Hz, 3H), 1.55-1.70 (m, 3H), 1.78-1.94 (m, 2H), 2.02-2.16 (m, 2H), 2.20-2.38 (m, 2H), 2.43 (d, J=5.4 Hz, 2H), 3.47-3.58 (m, 2H), 3.90-4.02 (m, 3H), 4.04 (t, J=5.8 Hz, 2H), 4.51 (d, J=11.1 Hz, 1H), 4.64 (d, J=11.1 Hz, 1H), 5.01 (q, J=6.6 Hz, 1H), 6.86 (d, J=8.5 Hz, 2H), 7.12 (s, 1H), 7.27 (d, J=8.5 Hz, 2H); $^{19}$F NMR (282.4 MHz, CDCl$_3$) δ −125.0 (2F), −122.2 (2F), −121.7 (2F), −120.7 (2F), −113.2 (2F), −79.6 (3F); $^{13}$C NMR (75 MHz, CDCl$_3$) δ −4.6, −4.5 (2C), −4.1, 14.1, 18.0, 18.3, 19.0, 22.7, 25.1, 25.6, 25.9, 26.0, 27.0, 28.0 (t, J$_{FC}$=22.2 Hz), 29.4, 29.6, 29.9, 31.9, 32.7, 33.1, 37.0, 66.3, 70.2, 72.7, 75.2, 77.4, 80.5, 82.0, 82.2, 105.3-120.3 (m, C$_6$F$_{13}$), 114.2, 129.4, 130.9, 131.9, 151.5, 158.0, 174.0.

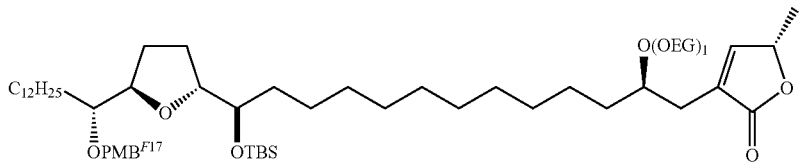

Global Detagging and Deprotecting in One Step:

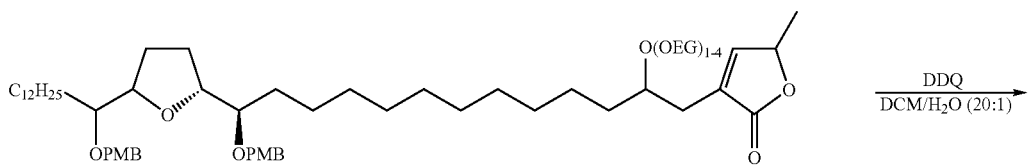

-continued

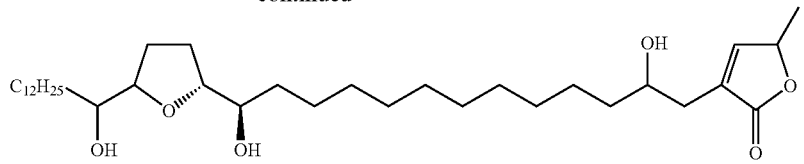

Doubly tagged butenolide was dissolved in $CH_2Cl_2/H_2O$ (1 mL/0.05 mL) and 2,3-dichloro-5,6-dicyano-1,4-benzoquinone (3.5 equiv) was added. The resulting mixture was stirred at room temperature for 1 h and then diluted with $CH_2Cl_2$ (5 mL) and brine (2 mL). The layers were separated and the aqueous layer was further extracted with $CH_2Cl_2$ (5×5 mL). The combined organic layers were washed with brine, dried over $MgSO_4$ and concentrated under vacuum. The residue was then directly subjected to prep-HPLC purification on chiralcel OD column to give the final product as white waxy solid. The coding of the tags with the configurations is shown in FIG. 11.

$^1$H NMR (600 MHz, $CDCl_3$) δ 0.89 (t, J=6.9 Hz, 3H), 1.24-1.32 (m, 36H), 1.32-1.42 (m, 3H), 1.44 (d, J=6.8 Hz, 3H), 1.45-1.53 (m, 3H), 1.66-1.69 (m, 1H), 1.72-1.79 (m, 2H), 1.91-1.99 (m, 2H), 2.41 (ddt, J=15.1 Hz, 8.9 Hz, 1.2 Hz, 1H), 2.54 (ddt, J=15.1 Hz, 3.4 Hz, 1.5 Hz, 1H), 3.41-3.44 (m, 2H), 3.80-3.87 (m, 3H), 5.07 (qq, J=6.6 Hz, 1.5 Hz, 1H), 7.19 (q, J=1.4 Hz, 1H); $^{13}$C NMR (151.1 MHz, $CDCl_3$) δ 14.20, 19.19, 22.77, 25.62, 25.73, 25.79, 28.20 (2C), 29.43, 29.51, 29.55, 29.58, 29.69, 29.71, 29.72, 29.74, 29.76, 29.78, 32.00,

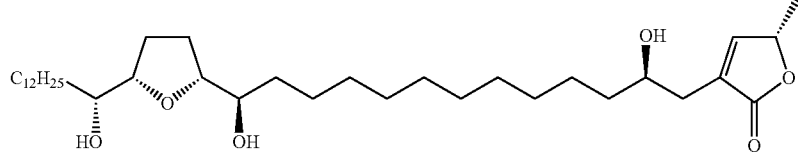

$^1$H NMR (600 MHz, $CDCl_3$) δ 0.89 (t, J=6.9 Hz, 3H), 1.24-1.35 (m, 36H), 1.36-1.41 (m, 2H), 1.44 (d, J=6.8 Hz, 3H), 1.45-1.53 (m, 6H), 1.59 (broad, 2H), 1.72-1.84 (m, 2H), 1.91-1.99 (m, 2H), 2.41 (dd, J=15.1 Hz, 8.3 Hz, 1H), 2.54 (ddt, J=15.2 Hz, 3.4 Hz, 1.5 Hz, 1H), 3.44-3.47 (m, 1H), 3.81-3.87 (m, 3H), 3.90-3.93 (m, 1H), 5.07 (qq, J=6.8 Hz, 1.5 Hz, 1H), 7.19 (q, J=1.4 Hz, 1H); $^{13}$C NMR (151.1 MHz, $CDCl_3$) δ 14.20, 19.20, 22.76, 24.40, 25.62, 25.77, 26.01, 28.49, 29.43, 29.49, 29.53, 29.55, 29.64, 29.66, 29.68, 29.73, 29.75, 31.99, 33.16, 33.43, 34.28, 37.48, 70.08, 72.41, 74.52, 78.05, 82.31, 82.76, 131.29, 151.86, 174.70; ESMS m/z: 603.4 (M+Na)$^+$, 581.4 (M+1)$^+$.

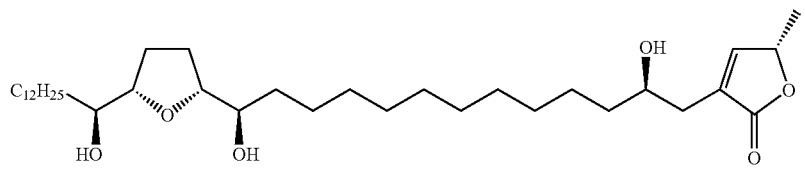

33.42, 34.16, 34.19, 37.49, 70.09, 74.46 (2C), 78.06, 82.75 (2C), 131.29, 151.87, 174.72; ESMS m/z: 619.5 (M+K)$^+$, 603.5 (M+Na)$^+$, 274.0.

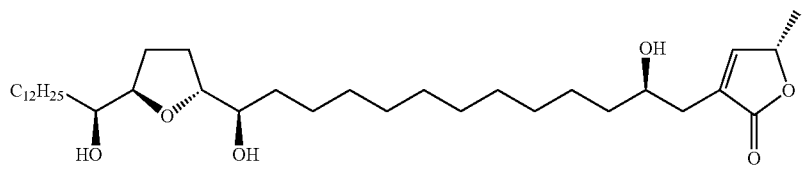

¹H NMR (600 MHz, CDCl₃) δ 0.89 (t, J=6.9 Hz, 3H), 1.24-1.34 (m, 36H), 1.35-1.42 (m, 5H), 1.44 (d, J=6.8 Hz, 3H), 1.46-1.55 (m, 5H), 1.83-1.95 (m, 2H), 1.98-2.04 (m, 1H), 2.41 (dd, J=15.1 Hz, 8.3 Hz, 1H), 2.54 (ddt, J=13.7 Hz, 3.3 Hz, 1.5 Hz, 1H), 3.40 (q, J=5.6 Hz, 1H), 3.80-3.90 (m, 4H), 5.07 (qd, J=6.9 Hz, 1.5 Hz, 1H), 7.19 (q, J=1.4 Hz, 1H); ¹³C NMR (151.1 MHz, CDCl₃) δ 14.20, 19.20, 22.77, 25.33, 25.64 (2C), 26.06, 28.67, 29.43, 29.56, 29.58, 29.60, 29.64, 29.68, 29.73, 29.75, 29.77, 32.00, 32.65, 33.33, 33.44, 37.51, 70.09, 71.64, 74.43, 78.05, 82.22, 83.30, 131.29, 151.85, 174.68; ESMS m/z: 619.4 (M+K)⁺, 603.4 (M+Na)⁺, 581.4 (M+1)⁺.

¹H NMR (600 MHz, CDCl₃) δ 0.89 (t, J=7.2 Hz, 3H), 1.27-1.40 (m, 36H), 1.44 (d, J=6.8 Hz, 3H), 1.46-1.51 (m, 6H), 1.66 (m, 3H), 1.73-1.76 (m, 2H), 1.93-1.97 (m, 2H), 2.41 (dd, J₁=15.1 Hz, J₂=8.3 Hz, 1H), 2.54 (d, J=15.1 Hz, 1H), 3.42-3.45 (m, 2H), 3.82-3.88 (m, 3H), 5.07 (qq, J₁=6.8 Hz, J₂=1.4 Hz, 1H), 7.19 (q, J=1.3 Hz, 1H); LC-MS (ESI) m/z: 619.5 (M+K)⁺, 603.5 (M+Na)⁺, 581.5 (M+1)⁺, 563.5 (M-OH)⁺, 545.5 (M-OH—H₂O)⁺, 527.5 (M-OH-2H₂O)⁺.

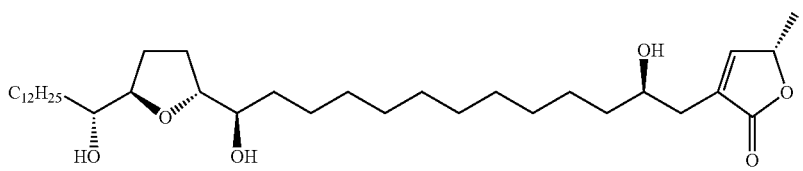

¹H NMR (600 MHz, CDCl₃) δ 0.89 (t, J=6.8 Hz, 3H), 1.24-1.38 (m, 36H), 1.39-1.43 (m, 4H), 1.44 (d, J=6.8 Hz, 3H), 1.45-1.54 (m, 5H), 1.64-1.72 (m, 2H), 1.96-2.02 (m, 2H), 2.41 (dd, J=15.1 Hz, 8.2 Hz, 1H), 2.53 (d, J=15.3 Hz, 1H), 3.40-3.43 (m, 2H), 3.79-3.86 (m, 3H), 5.07 (q, J=6.6 Hz, 1H), 7.19 (s, 1H); ¹³C NMR (151.1 MHz, CDCl₃) δ 14.20, 19.20, 22.77, 25.64 (2C), 25.68, 28.83 (2C), 29.43, 29.54, 29.57, 29.59, 29.67, 29.71, 29.72, 29.74, 29.75, 29.77, 29.79, 32.00, 33.43, 33.56 (2C), 37.50, 70.10, 74.13, 74.14, 78.06, 82.69, 82.71, 131.29, 151.86, 174.70; ESMS m/z: 619.5 (M+K)⁺, 603.5 (M+Na)⁺, 274.0.

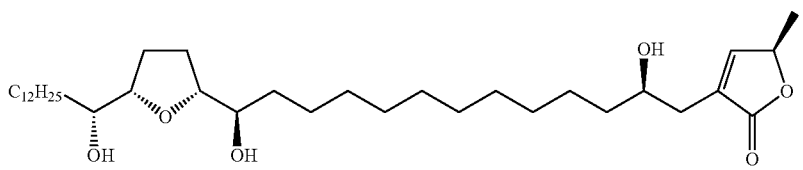

VG59-2-F5

¹H NMR (600 MHz, CDCl₃) δ 0.89 (t, J=7.1 Hz, 3H), 1.27-1.40 (m, 36H), 1.45 (m, 3H), 1.50 (m, 6H), 1.60 (m, 3H), 1.77-1.81 (m, 2H), 1.96 (m, 2H), 2.43 (m, 1H), 2.55 (d, J=14.5 Hz, 1H), 3.47 (m, 1H), 3.87 (m, 3H), 3.92 (m, 1H), 5.07 (m, 1H), 7.20 (m, 1H); LC-MS (ESI) m/z: 619.5 (M+K)⁺, 603.5 (M+Na)⁺, 581.5 (M+1)⁺, 563.5 (M-OH)⁺, 545.5 (M-OH—H₂O)⁺, 527.5 (M-OH-2H₂O)⁺.

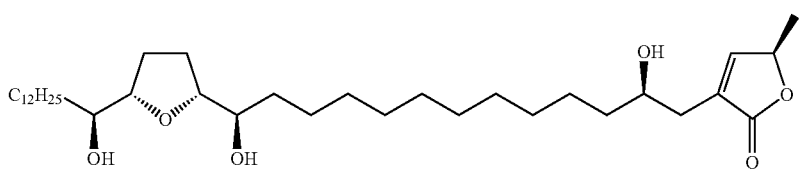

VG59-2-F9

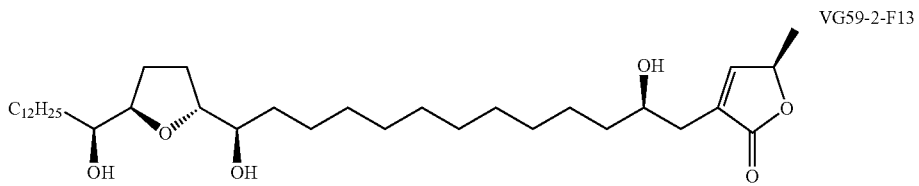

VG59-2-F13

¹H NMR (600 MHz, CDCl₃) δ 0.89 (t, J=7.1 Hz, 3H), 1.27-1.39 (m, 43H), 1.44 (d, J=6.7 Hz, 3H), 1.56 (m, 3H), 1.86-1.93 (m, 2H), 2.01 (m, 1H), 2.41 (dd, J₁=14.5 Hz, J₂=8.0 Hz, 1H), 2.54 (d, J=14.6 Hz, 1H), 3.40 (m, 1H), 3.83-3.84 (m, 4H), 5.07 (q, J=6.0 Hz, 1H), 7.19 (m, 1H); LC-MS (ESI) m/z: 619.5 (M+K)⁺, 603.5 (M+Na)⁺, 581.5 (M+1)⁺, 563.5 (M-OH)⁺, 545.5 (M-OH—H₂O)⁺, 527.5 (M-OH-2H₂O)⁺.

¹H NMR (600 MHz, CDCl₃) δ 0.90 (t, J=6.9 Hz, 3H), 1.28-1.32 (m, 34H), 1.39-1.41 (m, 2H), 1.46 (d, J=6.8 Hz, 3H), 1.50-1.53 (m, 6H), 1.59 (m, 3H), 1.75-1.84 (m, 2H), 1.94-2.01 (m, 2H), 2.43 (dd, J₁=15.1 Hz, J₂=8.2 Hz, 1H), 2.56 (d, J=15.6 Hz, 1H), 3.47-3.48 (m, 1H), 3.84-3.86 (m, 3H), 3.93 (m, 1H), 5.08 (q, J=6.5 Hz, 1H), 7.19 (m, 1H); LC-MS (ESI) m/z: 619.5 (M+K)⁺, 603.5 (M+Na)⁺, 581.5 (M+1)⁺,

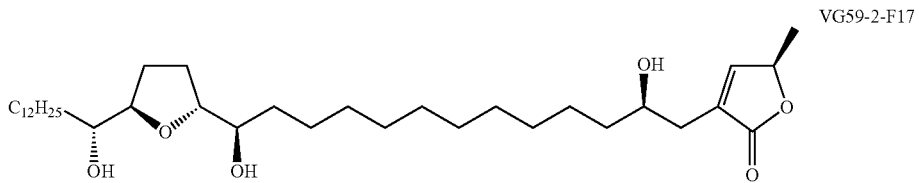

VG59-2-F17

¹H NMR (600 MHz, CDCl₃) δ 0.89 (t, J=7.1 Hz, 3H), 1.27-1.35 (m, 39H), 1.37-1.43 (m, 3H), 1.44 (d, J=6.8 Hz, 3H), 1.48-1.51 (m, 3H), 1.70 (m, 2H), 1.98-2.00 (m, 2H), 2.41 (dd, J₁=15.1 Hz, J₂=8.3 Hz, 1H), 2.54 (d, J=15.1 Hz, 1H), 3.41 (q, J=6.0 Hz, 2H), 3.81 (q, J=6.6 Hz, 4H), 3.83-3.86 (m, 1H), 5.07 (q, J=6.9 Hz, 1H), 7.19 (m, 1H); LC-MS (ESI) m/z: 619.5 (M+K)⁺, 603.5 (M+Na)⁺, 581.5 (M+1)⁺, 563.5 (M-OH)⁺, 545.5 (M-OH—H₂O)⁺, 527.5 (M-OH-2H₂O)⁺.

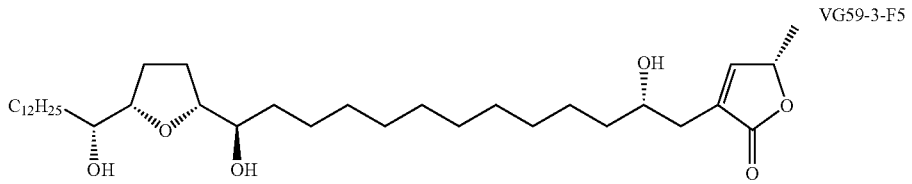

VG59-3-F5

563.5 (M-OH)⁺, 545.5 (M-OH—H₂O)⁺, 527.5 (M-OH-2H₂O)⁺.

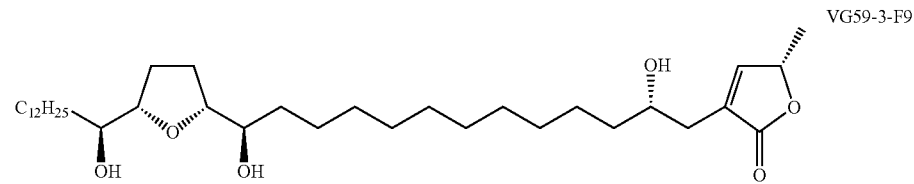

VG59-3-F9

¹H NMR (600 MHz, CDCl₃) δ 0.89 (t, J=6.8 Hz, 3H), 1.27-1.41 (m, 36H), 1.44 (d, J=6.5 Hz, 3H), 1.48 (m, 6H), 1.64 (m, 3H), 1.77 (m, 2H), 1.95 (m, 2H), 2.41 (dd, $J_1$=15.2 Hz, $J_2$=8.3 Hz, 1H), 2.54 (d, J=14.4 Hz, 1H), 3.44 (m, 2H), 3.85 (m, 3H), 5.07 (q, J=6.1 Hz, 1H), 7.19 (m, 1H); LC-MS (ESI) m/z: 619.5 (M+K)⁺, 603.5 (M+Na)⁺, 581.5 (M+1)⁺, 563.5 (M-OH)⁺, 545.5 (M-OH—H₂O)⁺, 527.5 (M-OH-2H₂O)⁺.

¹H NMR (600 MHz, CDCl₃) δ 0.89 (t, J=6.9 Hz, 3H), 1.26-1.34 (m, 34H), 1.37-1.39 (m, 3H), 1.44 (d, J=6.8 Hz, 3H), 1.47-1.51 (m, 5H), 1.61 (m, 3H), 1.73-1.83 (m, 2H), 1.92-1.99 (m, 2H), 2.40 (dd, $J_1$=15.2 Hz, $J_2$=8.3 Hz, 1H), 2.55 (d, J=15.2 Hz, 1H), 3.44-3.66 (m, 1H), 3.81-3.86 (m, 3H), 3.90-3.92 (m, 1H), 5.06 (qq, $J_1$=6.9 Hz, $J_2$=1.4 Hz, 1H), 7.19 (q, J=1.2 Hz, 1H); LC-MS (ESI) m/z: 619.5 (M+K)⁺, 603.5 (M+Na)⁺, 581.5 (M+1)⁺, 563.5 (M-OH)⁺, 545.5 (M-OH—H₂O)⁺, 527.5 (M-OH-2H₂O)⁺.

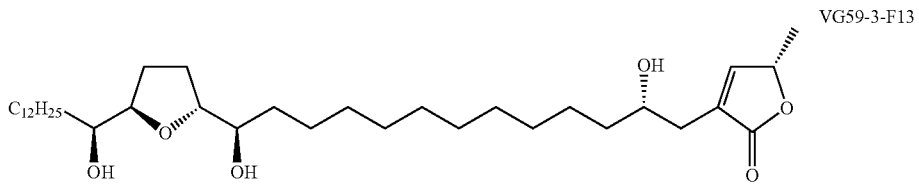

VG59-3-F13

¹H NMR (600 MHz, CDCl₃) δ 0.89 (t, J=6.9 Hz, 3H), 1.27-1.31 (m, 34H), 1.39 (m, 4H), 1.44 (d, J=6.8 Hz, 3H), 1.47-1.51 (m, 4H), 1.58-1.66 (m, 4H), 1.86-1.94 (m, 2H), 1.99-2.03 (m, 1H), 2.41 (dd, $J_1$=15.2 Hz, $J_2$=8.3 Hz, 1H), 2.54 (d, J=14.9 Hz, 1H), 3.40 (q, J=4.5 Hz, 1H), 3.82-3.88 (m, 4H), 5.07 (q, J=6.5 Hz, 1H), 7.19 (m, 1H); LC-MS (ESI) m/z: 619.5 (M+K)⁺, 603.5 (M+Na)⁺, 581.5 (M+1)⁺, 563.5 (M-OH)⁺, 545.5 (M-OH—H₂O)⁺, 527.5 (M-OH-2H₂O)⁺.

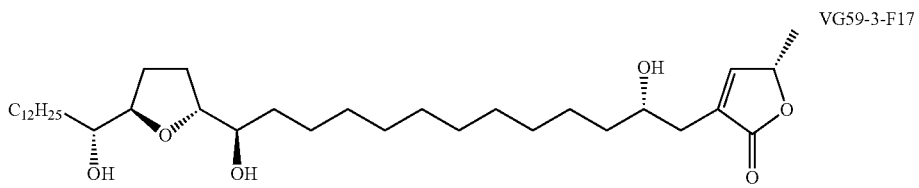

VG59-3-F17

¹H NMR (600 MHz, CDCl₃) δ 0.89 (t, J=7.0 Hz, 3H), 1.27-1.35 (m, 33H), 1.39-1.43 (m, 4H), 1.44 (d, J=6.8 Hz, 3H), 1.47-1.51 (m, 3H), 1.56 (m, 3H), 1.69-1.71 (m, 2H), 1.98-2.00 (m, 2H), 2.27 (m, 2H), 2.41 (dd, $J_1$=15.1 Hz, $J_2$=8.2 Hz, 1H), 2.54 (dt, $J_1$=15.1 Hz, $J_2$=1.6 Hz, 1H), 3.41 (q, J=6.0 Hz, 2H), 3.81 (q, J=6.4 Hz, 2H), 3.85-3.86 (m, 1H), 5.07 (q, J=6.3 Hz, 1H), 7.19 (m, 1H); LC-MS (ESI) m/z: 619.5 (M+K)⁺, 603.5 (M+Na)⁺, 581.5 (M+1)⁺, 563.5 (M-OH)⁺, 545.5 (M-OH—H₂O)⁺, 527.5 (M-OH-2H₂O)⁺.

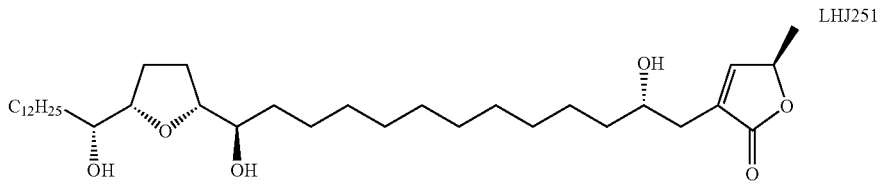

LHJ251

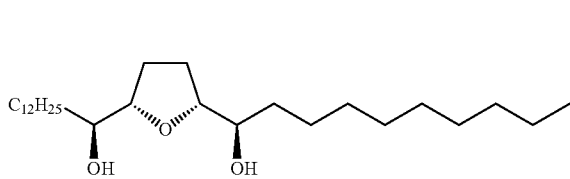

LHJ252

$^1$H NMR (600 MHz, CDCl$_3$) δ 0.89 (t, J=6.9 Hz, 3H), 1.27-1.41 (m, 36H), 1.44 (d, J=6.7 Hz, 3H), 1.48 (m, 6H), 1.62 (m, 3H), 1.77 (m, 2H), 1.95 (m, 2H), 2.40 (dd, J$_1$=14.5 Hz, J$_2$=7.6 Hz, 1H), 2.55 (d, J=14.6 Hz, 1H), 3.44 (m, 2H), 3.83 (m, 3H), 5.06 (q, J=6.5 Hz, 1H), 7.19 (m, 1H); LC-MS (ESI) m/z: 619.5 (M+K)$^+$, 603.5 (M+Na)$^+$, 581.5 (M+1)$^+$, 563.5 (M-OH)$^+$, 545.5 (M-OH—H$_2$O)$^+$, 527.5 (M-OH-2H$_2$O)$^+$.

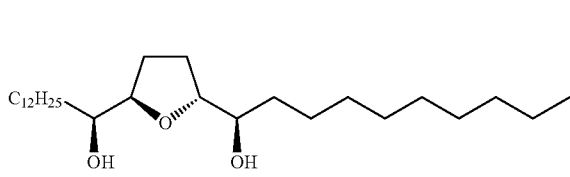

LHJ250

$^1$H NMR (600 MHz, CDCl$_3$) δ 0.89 (t, J=6.9 Hz, 3H), 1.27-1.30 (m, 34H), 1.37-1.41 (m, 4H), 1.44 (d, J=6.8 Hz, 3H), 1.48-1.52 (m, 4H), 1.60-1.66 (m, 3H), 1.84-1.99 (m, 2H), 2.00-2.03 (m, 2H), 2.40 (dd, J$_1$=15.0 Hz, J$_2$=8.4 Hz, 1H), 2.55 (d, J=14.9 Hz, 1H), 3.40-3.41 (m, 1H), 3.82-3.87 (m, 4H), 5.06 (q, J=6.8 Hz, 1H), 7.19 (m, 1H); LC-MS (ESI) m/z: 619.5 (M+K)$^+$, 603.5 (M+Na)$^+$, 581.5 (M+1)$^+$, 563.5 (M-OH)$^+$, 545.5 (M-OH—H$_2$O)$^+$, 527.5 (M-OH-2H$_2$O)$^+$.

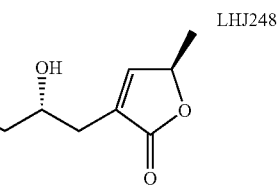

LHJ248

$^1$H NMR (600 MHz, CDCl$_3$) δ 0.89 (t, J=6.9 Hz, 3H), 1.27-1.28 (m, 37H), 1.41 (m, 4H), 1.44 (d, J=6.8 Hz, 3H), 1.48-1.50 (m, 4H), 1.66-1.70 (m, 2H), 2.00 (m, 2H), 2.41 (dd, J$_1$=15.2 Hz, J$_2$=8.3 Hz, 1H), 2.54 (d, J=15.7 Hz, 1H), 3.42 (m, 2H), 3.82-3.86 (m, 3H), 5.07 (q, J=6.7 Hz, 1H), 7.19 (m, 1H); LC-MS (ESI) m/z: 619.5 (M+K)$^+$, 603.5 (M+Na)$^+$, 581.5 (M+1)$^+$, 563.5 (M-OH)$^+$, 545.5 (M-OH—H$_2$O)$^+$, 527.5 (M-OH-2H$_2$O)$^+$.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A method of separating compounds, comprising:
    a. tagging at least a first organic compound with a first tagging moiety to result in a first tagged compound;
    b. tagging at least a second organic compound, different from the first organic compound, with a second tagging moiety different from the first tagging moiety to result in a second tagged compound, the first tagging moiety and the second tagging moiety including at least one of a common polar alkylene glycol repeat unit, but having a different number of the alkylene glycol repeat units therein, the greater the number of alkylene glycol repeat units, the greater the polarity of the tagging moiety, wherein the first tagging moiety and the second tagging moiety comprise between 1 and 20 alkylene glycol repeat units; and
    physically separating the first tagged compound from a mixture including at least the second tagged compound using a chromatographic separation technique dependent upon the number of alkylene glycol repeat units and thereby polarity.

2. The method of claim 1 wherein the first tagging moiety and the second tagging moiety are selected so that the order in which the first tagged compound and the second tagged compound separate is predetermined.

3. The method of claim 1 wherein the first tagging moiety and the second tagging moiety comprise between 1 and 5 repeat units.

4. The method of claim 1 wherein the repeat unit is an ethylene glycol repeat unit.

5. The method of claim 1 the stationary phase comprises a porous inorganic oxide, a mesoporous inorganic oxide, a porous polymer, or a mesoporous polymer.

6. The method of claim 1 wherein the stationary phase comprises silica gel, alumina, titania, or zirconia.

7. The method of claim 1 wherein the stationary phase is a silica gel.

8. The method of claim 1 wherein the stationary phase comprises a polar bonded phase of silica gel, alumina, titania, or zirconia.

9. The method of claim 1 wherein the stationary phase comprises a nonpolar bonded phase of silica gel, alumina, titania, or zirconia.

10. The method of claim 1 wherein a third compound having no repeat units is separated from the mixture using in the chromatographic separation technique.

11. The method of claim 1 wherein at least one of the first tagged compound and the second tagged compound also comprises a fluorous tagging moiety and the method further comprises a separation using a fluorous separation technique.

12. The method of claim 1 wherein the first tagged compound also includes a first fluorous tagging moiety and the second tagged compound also includes a second fluorous tagging moiety different from the first fluorous tagging moiety and the method further comprises a separation using a fluorous separation technique.

13. The method of claim 1 wherein at least one of the first tagged compound and the second tagged compound also comprises a alternative tagging moiety adapted to be separated via a second type of separation technique other than a separation technique based upon differences in polarity and the method further comprises a separation using the second type of separation technique.

14. The method of claim 1 wherein the first tagged compound also includes a first alternative tagging moiety adapted to be separated via a second type of separation technique other than a separation technique based upon differences in polarity and the second tagged compound comprises a second alternative tagging moiety different from the first alternative tagging moiety, the second alternative tagging moiety adapted to be separated via the second type of separation technique, and the method further comprises a separation using the second type of separation technique.

15. The method of claim 14 wherein the first tagging moiety and the first alternative tagging moiety are attached to the first compound via a common group or atom.

16. The method of claim 15 wherein the first tagging moiety and the first alternative tagging moiety are each attached to the common group that is attached to the first compound.

17. The method of claim 15 wherein the first tagging moiety and the first alternative tagging moiety are attached to each other and one of the first tagging moiety and the first alternative tagging moiety is attached to the first compound.

18. A method of separating compounds, the method comprising the steps of:
  a. tagging a first organic compound with a first tagging moiety to result in a first tagged compound;
  b. tagging at least a second organic compound, different from the first organic compound, with a second tagging moiety different from the first tagging moiety to result in a second tagged compound, the first tagging moiety and the second tagging moiety including at least one of a common alkylene glycol repeat unit, but having a different number of the alkylene glycol repeat units therein, the greater the number of alkylene glycol repeat units, the greater the polarity of the tagging moiety, wherein the first tagging moiety and the second tagging moiety comprise between 1 and 20 repeat units; and
  physically separating the first tagged compound into a predetermined fraction from a mixture including at least the second tagged compound using a separation technique dependent upon the number of alkylene glycol repeat units, wherein the predetermined fraction and the identity of the first tagged compound in the predetermined fraction are determined by the first tagging moiety.

19. The method of claim 18 wherein the first tagged compound and the second tagged compound are products in a chemical reaction.

* * * * *